(12) United States Patent
Schwab et al.

(10) Patent No.: US 10,442,773 B2
(45) Date of Patent: Oct. 15, 2019

(54) AMORPHOUS LETERMOVIR AND SOLID PHARMACEUTICAL FORMULATIONS THEREOF FOR ORAL ADMINISTRATION

(71) Applicant: AICURIS ANTI-INFECTIVE CURES GMBH, Wuppertal (DE)

(72) Inventors: Wilfried Schwab, Werder (DE); Dirk Jung, Dresden (DE); Christian Schickaneder, Lauf an der Pegnitz (DE); Welljanne Martens, Dresden (DE); Michael Limmert, Dresden (DE); Clemens Bothe, Leverkusen (DE); Mathias Berwe, Sprockhovel (DE); Nicole Rindermann, Bad Laer (DE)

(73) Assignee: AICURIS ANTI-INFECTIVE CURES GMBH, Wuppertal (DE)

(*) Notice: Subject to any disclaimer, the term of this patent is extended or adjusted under 35 U.S.C. 154(b) by 0 days.

(21) Appl. No.: 14/899,178

(22) PCT Filed: Jun. 19, 2014

(86) PCT No.: PCT/EP2014/062974
§ 371 (c)(1),
(2) Date: Dec. 17, 2015

(87) PCT Pub. No.: WO2014/202737
PCT Pub. Date: Dec. 24, 2014

(65) Prior Publication Data
US 2016/0145216 A1    May 26, 2016

(30) Foreign Application Priority Data

Jun. 19, 2013 (EP) .................................... 13003120
Apr. 16, 2014 (EP) .................................... 14165027

(51) Int. Cl.
| | | |
|---|---|---|
| *C07D 239/84* | (2006.01) |
| *A61P 31/00* | (2006.01) |
| *A61P 31/14* | (2006.01) |
| *A61P 31/18* | (2006.01) |
| *A61P 31/20* | (2006.01) |
| *A61P 31/12* | (2006.01) |
| *A61K 31/517* | (2006.01) |
| *A61K 9/00* | (2006.01) |
| *A61K 47/02* | (2006.01) |
| *A61K 47/12* | (2006.01) |
| *A61K 47/32* | (2006.01) |
| *A61K 47/38* | (2006.01) |

(52) U.S. Cl.
CPC .......... *C07D 239/84* (2013.01); *A61K 9/0053* (2013.01); *A61K 31/517* (2013.01); *A61K 47/02* (2013.01); *A61K 47/12* (2013.01); *A61K 47/32* (2013.01); *A61K 47/38* (2013.01); *A61P 31/00* (2018.01); *A61P 31/12* (2018.01); *A61P 31/14* (2018.01); *A61P 31/18* (2018.01); *A61P 31/20* (2018.01)

(58) Field of Classification Search
CPC ...... A61K 31/517; A61K 47/02; A61K 47/12; A61K 47/32; A61K 47/38; A61K 9/0053; C07D 239/84; A61P 31/00; A61P 31/12; A61P 31/14; A61P 31/18; A61P 31/20
USPC ..................................... 514/252.17; 544/284
See application file for complete search history.

(56) References Cited

U.S. PATENT DOCUMENTS

| | | |
|---|---|---|
| 8,084,604 B2 | 12/2011 | Goossen et al. |
| 8,372,972 B2 | 2/2013 | Goossen et al. |
| 8,816,075 B2 | 8/2014 | Goossen et al. |
| 2009/0221822 A1 | 9/2009 | Goossen et al. |
| 2012/0130072 A1 | 5/2012 | Goossen et al. |
| 2013/0066073 A1 | 3/2013 | Goossen et al. |
| 2015/0038514 A1 | 2/2015 | Grunenberg et al. |

(Continued)

FOREIGN PATENT DOCUMENTS

| | | |
|---|---|---|
| WO | 2006133822 A1 | 12/2006 |
| WO | 2013127971 A1 | 9/2013 |

OTHER PUBLICATIONS

International Search Report from PCT/EP2014/062974 dated Aug. 13, 2014.

(Continued)

*Primary Examiner* — My-Chau T. Tran
(74) *Attorney, Agent, or Firm* — Millen White Zelano and Branigan, PC; John Sopp

(57) ABSTRACT

The present invention provides for amorphous Letermovir and orally administrable solid pharmaceutical formulations thereof (immediate release formulation). Said amorphous Letermovir is suitable for immediate release formulations when isolated out of an organic solution by either roller-drying said organic solution in a volatile organic solvent, in particular acetone, at a temperature of 30° C. to 60° C., and subsequently drying the amorphous Letermovir obtained, or isolating said amorphous Letermovir by precipitation from water miscible solvents selected from acetone or acetonitrile into excess water as anti-solvent, and subsequently filtrating or centrifuging the amorphous Letermovir obtained.

The immediate release formulations of amorphous Letermovir are intended for use in methods of prophylaxis or methods of treatment of diseases associated with the group of Herpesviridae, preferably associated with cytomegalovirus (CMV), even more preferably associated with human cytomegalovirus (HCMV).

18 Claims, 15 Drawing Sheets

(56) References Cited

U.S. PATENT DOCUMENTS

2015/0050241 A1* 2/2015 Volinsky .............. A61K 31/522
424/85.6
2015/0133461 A1* 5/2015 Paulus ................. A61K 9/0019
514/252.17

OTHER PUBLICATIONS

P. Lischka et al. "In vitro and in vivo activities of the novel anticytomegalovirus compound AIC246" Antimicrobial Agents and Chemotherapy, [2010], vol. 54, No. 3, pp. 1290-1297.

* cited by examiner

| Entry | Experiment | Isolated Yield (%) | Isolated Residue (%)[1] | Morphology by XRPD | Comment |
|---|---|---|---|---|---|
| 1 | Distillative MTBE-removal with methanol. "Precipitation" by addition to water. | 90 | | amorphous | According to standard procedure. Good precipitation, comparable to acetone. |
| 2 | Distillative MTBE-removal with ethanol (water free, denaturated with toluene). "Precipitation" by addition to water. | 91 | | amorphous | According to standard procedure. Good precipitation, comparable to acetone. |
| 3 | Distillative MTBE-removal with acetonitrile. "Precipitation" by addition to water. | 91 | | amorphous | According to standard procedure. Good precipitation, comparable to acetone. |
| 4 | Distillative MTBE-removal with acetone. Product precipitation by addition to water. | 92 | | amorphous | Standard procedure. |
| 5 | Inverted precipitation: water addition to acetone solution. | 80 | | amorphous | Sticky material on flask wall; scraping off and further agitation was necessary in order to obtain solid material. |
| 6 | Inverted precipitation: water addition to acetonitrile solution. | 73 | | amorphous | Sticky material on flask wall; scraping off and further agitation was necessary in order to obtain solid material. |
| 7 | "Drum dryer-simulation": utilization of methanol | | 64 | amorphous | 60°C bath temperature; 300 --> 50 mbar, final foaming; residue scraped off the glass wall. |
| 8 | "Drum dryer-simulation": utilization of ethanol (water free; denaturated with toluene). | | 49 | amorphous | 60°C bath temperature; 250 --> 20 mbar, sudden foaming at 30 mbar; residue scraped off the glass wall. |
| 9 | "Drum dryer-simulation": utilization of acetonitrile. | | 49 | amorphous | 60°C bath temperature; 200 --> 20 mbar, final foaming; residue scraped off the glass wall. |
| 10 | "Drum dryer-simulation": utilization of DCM. | | 66 | amorphous | 60°C bath temperature; 900 --> 50 mbar, final foaming; residue scraped off the glass wall. |
| 11 | "Drum dryer-simulation": utilization of MTBE. | | 98 | amorphous | 60°C bath temperature; 800 --> 50 mbar, final foaming; residue scraped off the glass wall. |

FIG. 1

| Aqueous Media | Letermovir (mg/ml) |
|---|---|
| Water | 0.4 |
| 5 % Human serum albumin in water | 5.5 |

FIG.5

| Buffer pH | Letermovir (mg/ml) |
|---|---|
| pH 1 | 16.9 |
| pH 2 | 3.5 |
| pH 3 | 0.8 |
| pH 4 | 0.4 |
| pH 5 | 0.3 |
| pH 6 | 0.2 |
| pH 7 | 0.4 |
| pH 8 | 7.7 |
| pH 9 | 25.5 |
| pH 10 | 51.4 |
| pH 11 | 69.6 |
| pH 12 | 91.3 |

FIG.6

| Pharmacokinetics of Letermovir (mean ±SD, $t_{max}$: median [range]) | Cohort 1: 30 mg Letermovir 30 min iv infusion | Cohort 1: 30 mg Letermovir oral |
|---|---|---|
| n | 12[a] | 12[b] |
| $C_{max}$, ng/mL | 1209±235.3 | 363.5±118.4 |
| $t_{max}$, h | 0.50 (0.50-0.50) | 1.50 (1.00-3.00) |
| $AUC_{0-last}$, ng*h/mL | 1980±473.5 | 1544±478.9 |
| $AUC_{0-\infty}$, ng*h/mL | 2245[c]±353.4[c] | 1802[d]±298.8[d] |
| $\lambda z$, 1/h | 0.05837[c]±0.01335[c] | 0.04983[d]±0.01593[d] |
| $t_{1/2z}$, h | 12.66[c]±4.082[c] | 15.49[d]±5.869[d] |
| CL(/F), L/h | 13.66[c]±2.215[c] | 17.07[d]±2.857[d] |
| $V_D$ (/F), L | 251.5[c]±92.34[c] | 382.2[d]±175.2[d] |
| MRT, h | 5.543[c]±0.6608[c] | 8.509[d]±1.919[d] |

[a] n=8 for $AUC_{0-\infty}$, $\lambda z$, $t_{1/2term}$, CL, $V_D$ and MRT
[b] n=9 for $AUC_{0-\infty}$, ng*h/mL, $\lambda z$, $t_{1/2term}$, CL/F, $V_D$/F and MRT
[c] Accurate determination not possible in 4 subjects
[d] Accurate determination not possible in 6 subjects

FIG.7A

| Parameter | LS means | | LS means ratio, % | 90% CI, %[c] | p-value | | |
|---|---|---|---|---|---|---|---|
| | 30 mg Letermovir, 30 min iv infusion | 30 mg Letermovir, oral | | | period | sequence | treatment |
| $AUC_{0-last}$, ng*h/mL[a] | 1924 | 1459 | 76.82 | 68.40-84.04 | 0.4707 | 0.4719 | 0.0006* |
| $AUC_{0-\infty}$, ng*h/mL[b] | 2158 | 1771 | 82.07 | 74.53-90.37 | 0.2929 | 0.1322 | 0.0072* |

[a] n=12 for 30 min iv infusion and oral Letermovir
[b] n=8 for 30 min iv infusion and oral Letermovir
[c] 90% confidence intervals
* Statistically significant difference

FIG.7B

| Drug Product: | Letermovir 240 mg USA/EU FCT | | | | | | | | Batch No.: 4100601T | |
|---|---|---|---|---|---|---|---|---|---|---|
| Dosage: | 240 mg | | | | | | | | Packaging: | |
| Storage condition: | 25°C ± 2°C / 60% RH ± 5% RH | | | | | | | | Brown bottles of glass with 30 FCT | |

| Test Item | Specification | T0 | t3 | t6 | t9 | t12 | t18 | t24 | t36 |
|---|---|---|---|---|---|---|---|---|---|
| Appearance | yellow/ochre, round tablets without markings | complies | complies | complies | complies | complies | complies | complies | complies |
| Water content [%] | for information | 2.60 | 2.17 | 2.08 | 1.86 | 3.97 | 1.98 | 2.17 | 2.62 |
| Identity | the retention time of AIC-001 must comply with the reference sample | complies | complies | complies | complies | complies | complies | complies | complies |
| Assay [mg/dosi] | 216.0 - 264.0 | 249.9 | 240.2 | 240.5 | 243.4 | 240.4 | 242.0 | 236.8 | 238.7 |
| Impurities [%] | | | | | | | | | |
| unknown, single | ≤ 0.6 | 0.1 | 0.1 | 0.1 | 0.1 | 0.1 | 0.0 | 0.0 | 0.0 |
| total | ≤ 3.0 | 0.1 | 0.1 | 0.1 | 0.1 | 0.1 | 0.0 | 0.0 | 0.0 |
| Enantiomeric excess [%] | for information | not performed | not performed | not performed | not performed | not performed | 99.8 | 99.8 | 99.8 |
| Dissolution [%] | | | | | | | | | |
| 15 min | for information | 84 | 88 | 89 | 90 | 89 | 91 | 85 | 86 |
| 30 min | ≥ 80 (minimum value - Level 1), ≥ 75 (average value - Level 2), ≥ 60 (minimum value - Level 2) | 87 | 93 | 93 | 94 | 95 | 93 | 92 | 90 |
| 45 min | for information | 89 | 94 | 93 | 97 | 96 | 94 | 93 | not requested |
| Microbial purity | | | | | | | | | |
| bacteria | ≤ 10³ cfu/g | not requested | not requested | not requested | not requested | not requested | not requested | not requested | not requested |
| yeast / fungi | ≤ 10² cfu/g | not requested | not requested | not requested | not requested | not requested | not requested | not requested | not requested |
| Bile-tolerant gram-negative bacteria | ≤ 10² cfu/g | not requested | not requested | not requested | not requested | not requested | not requested | not requested | not requested |
| E. coli | absent in 1 g | not requested | not requested | not requested | not requested | not requested | not requested | not requested | not requested |
| Salmonella | absent in 10 g | not requested | not requested | not requested | not requested | not requested | not requested | not requested | not requested |
| Staphylococcus aureus | absent in 1 g | not requested | not requested | not requested | not requested | not requested | not requested | not requested | not requested |

FIG. 8A

| Drug Product: | Letermovir 60 mg USA/EU FCT | | | | | | | | | |
|---|---|---|---|---|---|---|---|---|---|---|
| Dosage: | 60 mg | | | | | Batch No.: 41006011 | | | | |
| Storage condition: | 25°C ± 2°C / 60% RH ± 5% RH | | | | | Packaging: Brown bottles of glass with 100 FCT | | | | |

| Test Item | Specification | T0 | t3 | t6 | t9 | t12 | t18 | t24 | t36 |
|---|---|---|---|---|---|---|---|---|---|
| Appearance | yellow/ochre, round tablets without markings | complies | complies | complies | complies | complies | complies | complies | complies |
| Water content [%] | for information | 2.20 | 2.23 | 1.78 | 1.85 | 3.30 | 1.74 | 2.14 | 3.17 |
| Identity | the retention time of A/C-001 must comply with the reference sample | complies | complies | complies | complies | complies | complies | complies | complies |
| Assay [mg/dose] | 54.0 - 66.0 | 60.3 | 60.4 | 61.3 | 62.2 | 61.6 | 61.9 | 60.0 | 59.3 |
| Impurities [%] | | | | | | | | | |
| unknown, single | ≤ 0.6 | 0.0 | 0.1 | 0.0 | 0.1 | 0.0 | 0.0 | 0.1 | 0.0 |
| total | ≤ 3.0 | 0.0 | 0.2 | 0.0 | 0.1 | 0.0 | 0.0 | 0.1 | 0.0 |
| Enantiomeric excess [%] | for information | not requested | not requested | not requested | not requested | not requested | not requested | 99.8 | 99.8 |
| Dissolution [%] | | | | | | | | | |
| 15 min | for information | 58 | 55 | 51 | 55 | 56 | 62 | 57 | 49 |
| 30 min | ≥ 80 (minimum value - Level 1), ≥ 75 (average value - Level 2), ≥ 60 (minimum value - Level 2) | 93 | 95 | 95 | 96 | 96 | 96 | 95 | 95 |
| 45 min | for information | 96 | 96 | 97 | 99 | 99 | 97 | 96 | not requested |
| Microbial purity | | | | | | | | | |
| bacteria | ≤ 10³ cfu/g | not requested | not requested | not requested | not requested | not requested | not requested | not requested | not requested |
| yeast / fungi | ≤ 10² cfu/g | not requested | not requested | not requested | not requested | not requested | not requested | not requested | not requested |
| Bile-tolerant gram-negative bacteria | ≤ 10² cfu/g | not requested | not requested | not requested | not requested | not requested | not requested | not requested | not requested |
| E. coli | absent in 1 g | not requested | not requested | not requested | not requested | not requested | not requested | not requested | not requested |
| Salmonella | absent in 10 g | not requested | not requested | not requested | not requested | not requested | not requested | not requested | not requested |
| Staphyloccocus aureus | absent in 1 g | not requested | not requested | not requested | not requested | not requested | not requested | not requested | not requested |

FIG. 8B

| Drug Product: | Letermovir 120 mg USA/EU FCT | | | | | | | | | Batch No.: 4100701T | |
| --- | --- | --- | --- | --- | --- | --- | --- | --- | --- | --- | --- |
| Dosage: | 120 mg | | | | | | | | | Packaging: | |
| Storage condition: | 25°C ± 2°C / 60% RH ± 5% RH | | | | | | | | | Brown bottles of glass with 60 FCT | |

| Test Item | Specification | T0 | t3 | t6 | t9 | t12 | t18 | t24 | t36 |
| --- | --- | --- | --- | --- | --- | --- | --- | --- | --- |
| Appearance | yellow/ochre, round tablets without markings | complies | complies | complies | complies | complies | complies | complies | complies |
| Water content [%] | for information | 2.30 | 2.07 | 1.95 | 2.03 | 3.62 | 1.82 | 2.12 | 2.60 |
| Identity | the retention time of AIC-001 must comply with the reference sample | complies | complies | complies | complies | complies | complies | complies | complies |
| Assay [mg/dose] | 108.0 – 132.0 | 119.8 | 120.2 | 119.7 | 120.3 | 121.0 | 121.6 | 119.3 | 118.5 |
| impurities [%] | | | | | | | | | |
| unknown, single | ≤ 0.6 | 0.1 | 0.1 | 0.0 | 0.0 | 0.0 | 0.0 | 0.0 | 0.0 |
| total | ≤ 3.0 | 0.1 | 0.1 | 0.0 | 0.0 | 0.0 | 0.0 | 0.0 | 0.0 |
| Enantiomeric excess [%] | for information | not requested | not requested | not requested | not requested | not requested | not requested | 99.8 | 99.8 |
| Dissolution [%] | | | | | | | | | |
| 15 min | for information | 85 | 84 | 84 | 88 | 79 | 82 | 83 | 77 |
| 30 min | ≥ 80 (minimum value - Level 1), ≥ 75 (average value - Level 2), ≥ 60 (minimum value - Level 2) | 93 | 95 | 94 | 99 | 94 | 93 | 92 | 94 |
| 45 min | for information | 95 | 95 | 94 | 100 | 96 | 95 | 94 | not requested |
| Microbial purity | | | | | | | | | |
| bacteria | ≤ 10³ cfu/g | not requested | not requested | not requested | not requested | not requested | not requested | not requested | not requested |
| yeast / fungi | ≤ 10² cfu/g | not requested | not requested | not requested | not requested | not requested | not requested | not requested | not requested |
| Bile-tolerant gram-negative bacteria | ≤ 10² cfu/g | not requested | not requested | not requested | not requested | not requested | not requested | not requested | not requested |
| E. coli | absent in 1 g | not requested | not requested | not requested | not requested | not requested | not requested | not requested | not requested |
| Salmonella | absent in 10 g | not requested | not requested | not requested | not requested | not requested | not requested | not requested | not requested |
| Staphylococcus aureus | absent in 1 g | not requested | not requested | not requested | not requested | not requested | not requested | not requested | not requested |

FIG. 8C

| Test Parameters/Specification | Initial | 12 months | 24 months | 36 months | Valuation |
|---|---|---|---|---|---|
| Appearance white to yellow or brown solid | white solid | white solid | almost white solid | white solid | no change |
| Purity Related substances HPLC * | | | | | |
| Di-p-toluoyl tartaric acid ≤ 0.10% | 0.01% | <0.01% | <0.01% | <0.05% (<0.01%) | no change |
| Quinazolylpiperazine ≤ 0.10% | <0.01% | 0.01% | 0.01% | <0.05% (0.01%) | no change |
| Quinazolyldipiperazine ≤ 0.10% | 0.01% | 0.01% | <0.02% | <0.05% (0.02%) | no change |
| each unspecified impurity ≤ 0.10% | RRT    % <0.01% | RRT    % 1.10  0.01 1.65  0.01 | RRT    % 0.86  0.01 1.09  0.01 1.53  0.01 | RRT    % 0.84  (0.01) 1.09  (0.01) | no change |
| RRT – relative retention time reacting level: 0.01% (until 24 month) / 0.05% | | | | | |
| Total ≤ 1.5% | 0.02% | 0.04% | 0.06% | <0.05% | no change |
| Purity Enantiomeric excess (HPLC) EE ≥ 98.8% | 99.9% | 99.9% | 99.9% | 99.9% | no change |
| Purity Water content | 1.05% | 0.78% | 0.83% | 0.77% | no change |
| Purity Appearance of the solution ≤ BY₅ or Y₅ or B₃ | <BY₅, <Y₅, <B₃ | next > BY₅, next Y₅, <B₃ | next BY₅, next Y₅, between B₃ and B₂ | <BY₅, next B₂ | no change |
| Assay HPLC 97.0% – 102.0%, calculated to anhydrous and solvent free substance | 99.5% | 99.2% | 98.6% | 98.2% | no change |
| Microbiological purity | conforms | not tested | not tested | not tested | – |

FIG. 10

| Test Parameters | initial | 3 months | 6 months | 9 months | 12 months | 18 months | 24 months | 36 months | 48 months | Valuation |
|---|---|---|---|---|---|---|---|---|---|---|
| Appearance white to yellow or brown solid | almost white solid | white solid | almost white solid | almost white solid | almost white solid | white solid | white solid | white solid | white solid | no change |
| Purity Related substances HPLC * | | | | | | | | | | |
| Di-p-toluoyl tartaric acid ≤ 0.10% | 0.04% | < 0.01% | < 0.01% | < 0.01% | < 0.01% | < 0.01% | 0.01% | < 0.01% | < 0.01% | |
| Quinazolylpiperazine ≤ 0.10% | 0.02% | 0.03% | 0.03% | < 0.01% | 0.02% | 0.02% | 0.02% | 0.03% | 0.03% | |
| Quinazolyldipiperazine ≤ 0.10% | < 0.01% | < 0.01% | < 0.01% | < 0.01% | < 0.01% | < 0.01% | < 0.01% | < 0.01% | < 0.01% | |
| each unspecified impurity ≤ 0.10%   rel. RT | | | | | | | | | | |
| 0.52 | < 0.01% | < 0.01% | < 0.01% | 0.01% | < 0.01% | < 0.01% | < 0.01% | < 0.01% | 0.01% | |
| 0.84 | < 0.01% | 0.02% | 0.02% | 0.01% | 0.01% | < 0.01% | < 0.01% | 0.01% | 0.01% | |
| 1.10 | 0.01% | 0.03% | 0.03% | 0.03% | 0.02% | 0.01% | < 0.01% | 0.01% | 0.01% | |
| 1.13 | < 0.01% | < 0.01% | < 0.01% | < 0.01% | < 0.01% | < 0.01% | < 0.01% | < 0.01% | 0.02% | |
| 1.21 | 0.01% | < 0.01% | < 0.01% | 0.03% | < 0.01% | 0.03% | < 0.01% | 0.03% | 0.02% | |
| 1.56 | < 0.01% | < 0.01% | < 0.01% | 0.01% | < 0.01% | < 0.01% | < 0.01% | < 0.01% | < 0.01% | |
| 1.63 | < 0.01% | < 0.01% | 0.01% | < 0.01% | < 0.01% | < 0.01% | < 0.01% | < 0.01% | 0.02% | |
| | | | | | | | | | 0.01% | |
| Total ≤ 1.5% | 0.06% | 0.09% | 0.10% | 0.08% | 0.04% | 0.06% | 0.04% | 0.10% | 0.13% | no significant changes |
| Enantiomeric excess (HPLC) EE ≥ 98.8% | 99.9% | 99.9% | 99.9% | 99.8% | 99.8% | 99.8% | 99.8% | 99.8% | 99.8% | no change |
| Water content < 2.0% | 0.92% | 0.63% | 0.62% | 0.51% | 0.73% | 0.36% | 0.48% | 0.53% | 0.51% | slight decrease |
| Appearance of the solution ≤ BY₅ or Y₅ or B₅ | < BY₃, < Y₅, < B₇ | = BY₇, < Y₅, < B₇ | < BY₇, next Y₅, < B₇ | < BY₇, next Y₅, < B₇ | < BY₇, next Y₅, = B₇ | < BY₇, next Y₅, = B₇ | < BY₇, next Y₅, = B₇ | < BY₇, next Y₅, = B₇ | < BY₇, next Y₅, = B₇ | no change |
| Assay HPLC 97.0% - 102.0% water and solvent-free substance | 100.7% | 100.8% | 99.8% | 101.2% | 99.6% | 99.8% | 100.4% | 98.4% | 101.1% | no change |

\* reporting level: 0.01%

FIG. 11

AMORPHOUS LETERMOVIR AND SOLID PHARMACEUTICAL FORMULATIONS THEREOF FOR ORAL ADMINISTRATION

FIELD OF THE INVENTION

The technical field of the invention is pharmaceutical chemistry/galenic formulation. The present invention is related to new stable galenic formulations of the amorphous compound Letermovir for oral administration. Said formulations are suitable for use as orally administered pharmaceuticals in methods of treatment of viral diseases, in particular human cytomegalovirus (hereinafter HCMV) infections. The invention also relates to processes for isolating Letermovir as active pharmaceutical ingredient (hereinafter API) in the amorphous state. Specifically, the present invention relates to amorphous Letermovir having advantageous physicochemical properties with respect to particle size distribution, specific surface area and toxic impurity content, which makes the compound ready to be formulated in a solid pharmaceutical formulation for oral administration.

BACKGROUND

It is well known that an API in the amorphous state present the pharmaceutical industry with problems that have to be faced during isolation and galenic formulation thereof. Particularly zwitterionic compounds such as Letermovir, known for occurring in different salt forms, provide for many challenges during synthesis and galenic formulation.

Letermovir is known as an highly active drug for addressing HCMV infection and extensively described in Lischka et al., *In Vitro and In Vivo Activities of the Novel Anticytomegalovirus Compound Letermovir. Antimicrob. Agents Chemother.* 2010, 54: p. 1290-1297, and Kaul et al., *First report of successful treatment of multidrug-resistant cytomegalovirus disease with the novel anti-CMV compound Letermovir. Am. J. Transplant.* 2011, 11:1079-1084; as well as Marschall et al., *In Vitro Evaluation of the Activities of the Novel Anticytomegalovirus Compound Letermovir against Herpesviruses and Other Human Pathogenic Viruses. Antimicrob. Agents Chemother.* 2012, 56:1135-1137.

HCMV is a species of virus that belongs to the viral family known as Herpesviridae or herpes viruses. It is typically abbreviated as HCMV and is alternatively known as human herpesvirus-5 (HHV-5). Within Herpesviridae, HCMV belongs to the Betaherpesvirinae subfamily, which also includes cytomegaloviruses from other mammals.

Although they may be found throughout the body, HCMV infections are frequently associated with the salivary glands. HCMV infection is typically unnoticed in healthy people, but can be life-threatening for immuno-compromised subjects, such as HIV infected persons, organ transplant recipients, or newborn infants. In particular, HCMV remains the leading viral cause of birth defects and life-threatening disease in transplant recipients.

Currently approved anti-HCMV drugs target the viral DNA polymerase, pUL54. The known compound Ganciclovir (GCV) acts as nucleoside analogue. Its antiviral activity requires phosphorylation by the HCMV protein kinase, pUL97. In this regard, Cidovir (CDV) as a nucleotide analogue is already phosphorylated and thus active. Foscarnet (FOS) has a different mode of action. It directly inhibits polymerase function by blocking the pyrophosphate binding site of pUL54. However, the above drugs are known to be associated with toxicity and the emergence of drug resistance. Further, its bioavailability remains improvable.

Attempts have been made to develop orally more active, less toxic HCMV antiviral drugs accompanied with a new mode of action by the synthesis and evaluation of benzimidazole ribonucleosides. Drugs of this class were shown to be highly active against HCMV and targeting the viral terminase complex. However, it turned out that such compounds were metabolically unstable.

Furthermore, HCMVs resistant to benzimidazole ribonucleosides have been described where the resistance has been mapped to the viral open reading frames (hereinafter ORFs) UL89 and UL56 (cf. Krosky et al., *Resistance of Human Cytomegalovirus to Benzimidazole Ribonucleosides-Maps to Two Open Reading Frames: UL89 and UL56, Journal of Virology,* 1998, p. 4721-4728, and Evers et al., *Inhibition of Human Cytomegalovirus Replication by Benzimidazole Nucleosides Involves Three Distinct Mechanisms, Antimicrobial Agents and Chemotherapy,* 2004, p. 3918-3927).

BAY 38-4766 is another potent and selective inhibitor of HCMV replication and a representative of a novel non-nucleosidic class of anti-HCMV-drugs, the phenylenediamine sulfonamides. It also targets the viral terminase complex. BAY 38-4766 prevents the cleavage of high molecular weight viral DNA concatemers to monomeric genomic lengths. However, the development of such compounds was discontinued.

Furthermore, compound resistant HCMVs have been described, which inter alia contain mutations in the viral ORFs UL56 and UL89 (cf. Buerger et al., *A Novel Non-nucleoside Inhibitor Specifically Targets Cytomegalovirus DNA Maturation via the UL89 and UL56 Gene Products, Journal of Virology,* 2001, p. 9077-9086).

Other attempts to discover improved anti-HCMV drugs led to the identification of the small-molecular-weight compounds Bay 82-3286 and 3,4 dihydroquinazolines, such as Letermovir.

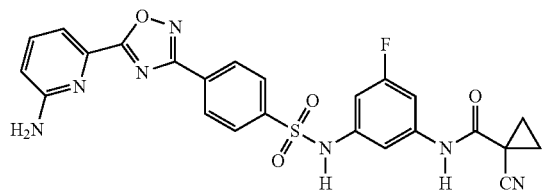

CSM: BAY 82-3286

By contrast to the above-described compounds, the 3,4 dihydroquinazolines as Letermovir block the viral replication without inhibiting the synthesis of progeny HCMV DNA or viral proteins. In fact, Letermovir was shown to act via a mode of action that involves the viral terminase. However, its mode of interaction with the viral terminase complex and its chemical structure is distinct from that of all other thus-far characterized drugs that were known to target the HCMV terminase complex, including BDCRB and BAY 38-4766. While an antiviral activity against rodent cytomegaloviruses was described for all published cleavage/packaging inhibitors, including BDCRB and BAY 38-4766, Letermovir is solely active against the human cytomegalovirus and thus poses high potential as specific human anti-HCMV drug.

The precise chemical name of Letermovir is (S)-{8-Fluoro-2-[4-(3-methoxyphenyl)-1-piperazinyl]-3-[2-methoxy-5-(trifluoromethyl)phenyl]-3,4-dihydro-4-quinazolinyl}acetic acid, having the Formula (I) as depicted below Formula (I)

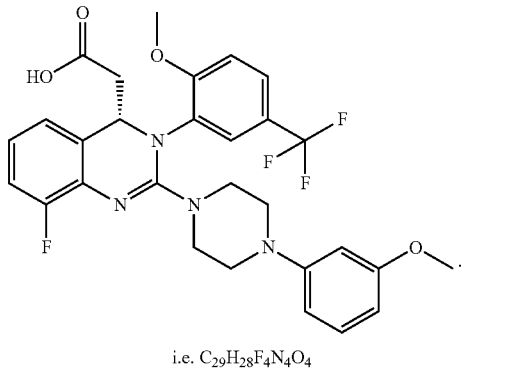

i.e. $C_{29}H_{28}F_4N_4O_4$

The synthesis of Letermovir is disclosed in US 2007/0191387 A1, exemplary embodiments 14 and 15, pages 40 and 41, paragraphs [0495] to [0505]. Letermovir exhibits a superior anti-HCMV activity in vitro and in vivo and has completed clinical phase IIb trial.

US 2007/0191387 A1 is silent about particular physicochemical properties of Letermovir as regards particle size distribution, specific surface area and pharmaceutically acceptable impurity contents that makes it suitable for solid galenic formulations that are orally administrable.

Preparation of Letermovir is described in WO 2006/133822; Example 11.

WO 2006/133822 is silent about particular physicochemical properties of Letermovir as regards particle size distribution, specific surface area and pharmaceutically acceptable impurity contents that makes it suitable for solid galenic formulations that are orally administrable.

WO 2013/127971 A1 describes sodium and calcium salts of Letermovir and solvates thereof, and use thereof as antiviral agents. WO 2013/127971 A1 is silent about particular physicochemical properties of Letermovir as regards particle size distribution, specific surface area and pharmaceutically acceptable impurity contents that makes it suitable for solid galenic formulations that are orally administrable.

Letermovir inhibits HCMV replication through a specific antiviral mechanism that involves the viral terminase subunit, but that is distinct from that of other compound classes also known to target this enzyme complex (cf. Goldner et al., *The Novel Anticytomegalovirus Compound AIC246 (Letermovir) Inhibits Human Cytomegalovirus Replication through a Specific Antiviral Mechanism That Involves the Viral Terminase, Journal of Virology*, 2011, p. 10884-10893).

However, the zwitterionic Letermovir bears chemical properties that pose challenges in the field of pharmaceutical chemistry. Following this, isolated Letermovir as zwitterion can be kept in an amorphous state, whereas in the form of acid and basic salts, Letermovir is crystallizable with a limited number of counter ions (see also German Patent Application 10 2012 101 673.9; German Patent Application 10 2012 101 659.3).

Attempts to crystallize the API Letermovir reproducibly in zwitterionic form and to keep it crystallized as a stable polymorph have failed to date. Hence, Letermovir has to be isolated in its amorphous state by sufficient yield and purity while conserving its physicochemical properties, which enable sufficient dissolution characteristics to be implemented in a tablet/capsule formulation for oral administration.

In this regard, only solution formulations of Letermovir are known in the art. However, amorphous Letermovir for intravenously applicable formulations were only completely soluble in water (w/w and w/o ethanol) by adding excess arginine or lysine, or the addition of cyclodextrin in combination with sodium hydroxide.

It was the object of the present invention to obtain fast dissolving solid dosage forms such as tablets and/or capsules of Letermovir in the amorphous state suitable for oral administration. In this context, it was a further object of the invention to obtain oral dosage forms of the solid amorphous API Letermovir for oral administration having sufficient bioavailability.

However, wet granulations based on an aqueous solution of Letermovir and excess arginine by using both, spray and high shear granulation did not result in a tablet/capsule that exhibit sufficient dissolution for immediate release (hereinafter IR). In particular, problems were encountered with respect to isolation of Letermovir as a pure API, purity and/or chemical stability were insufficient in case of most organic solvents including lower alcohols. Thus, against expectation the approach for intravenous formulations by adding arginine was not transferable to tablet/capsule formulations of Letermovir. Arginine did not have a positive effect on the dissolution properties of Letermovir in solid dosage forms as shown in Example 1.

A solubility study conducted by the inventors also confirmed the problematic solubility profile of amorphous Letermovir as in the pH-range of 1 to 7.5 Letermovir solubility varied from 0.4 to >1 mg/ml as shown in Example 2.

BRIEF DESCRIPTION OF THE INVENTION

Surprisingly and unexpectedly, the present invention provides for a pure API Letermovir in the amorphous state that is sufficient for further processing towards solid pharmaceutical formulations for oral administration. The herein provided solid pharmaceutical formulations enable dissolution properties of the amorphous Letermovir in a granulated formulation of >50% within 30 minutes, when tested for dissolution using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 30 minutes as follows:

HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention time: 1.3 minutes
Column temperature: 40° C.
Injection volume: 20 μL
Flow rate: 1.5 ml/min
Mobile phase: Buffer pH 4.0/Acetonitrile; 55/45 v/v.

Accordingly, a high degree of oral bioavailability may be expected based on said improved dissolution properties.

In a first major aspect the inventors found that amorphous Letermovir can be favorably isolated by either i) roller-drying of a solution of amorphous Letermovir in a volatile organic solvent, preferably acetone, or ii) precipitation of the amorphous Letermovir from water miscible solvents (preferably acetone or acetonitrile) into excess water as anti-solvent.

In principle, amorphous compounds such as Letermovir can be also isolated by spray drying or evaporation of a solution in an organic solvent, but in case of Letermovir yields and/or purity were insufficient due to huge amounts of residual solvent remaining in the amorphous API Letermovir.

In a second major aspect the inventors found two preferred methods for manufacture, i.e. in case of Letermovir isolated on a roller dryer that the API is preferably processed using wet granulation and in case of precipitated Letermovir, the API is preferably processed using dry granulation.

Both processes enable the manufacture of galenic formulations of amorphous Letermovir as API that are reproducible and exhibit dissolution properties of Letermovir in granulation formulation of >50% within 30 minutes, when tested for dissolution using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 30 minutes as follows:

HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention time: 1.3 minutes
Column temperature: 40° C.
Injection volume: 20 μL
Flow rate: 1.5 ml/min
Mobile phase: Buffer pH 4.0/Acetonitrile; 55/45 v/v.

DETAILED DESCRIPTION OF THE INVENTION

The present invention relates to an improved isolation of the amorphous API Letermovir and chemically stable galenic formulations thereof having sufficient dissolution properties for oral administration. Further, the present invention relates to oral dosage forms such as tablets or capsules that contain the solid amorphous API Letermovir or pharmaceutically acceptable salts, solvates or hydrates thereof and exhibit sufficient bioavailability thereof. Moreover, the present invention relates to orally applicable pharmaceutical formulations of the solid amorphous API Letermovir or pharmaceutically acceptable salts, solvates or hydrates thereof for use in methods of treatment of viral diseases, in particular in methods of treatment for HCMV infections.

With the context of the present invention, problems to be faced for appropriate galenic formulations based on amorphous Letermovir are reflected by a) its inescapable isolation out of a solution in an organic solvent so to obtain amorphous Letermovir in a pure form exhibiting physicochemical properties sufficient for preparation of oral formulations, and b) the provision of adequate galenic formulations that keep Letermovir in the amorphous state, and enable IR tablet or capsule granulations.

In regard to item a) above, the FIG. 12 shows a reaction scheme for the preferred synthetic route of Letermovir. Therein, the asterisk on the bottom left before step 4)—solvent switch indicates the step where the isolation pursuant to the invention initiates.

In this regard the present invention provides the solution to the above problems underlying the invention, namely to a) the provision of adequate isolation techniques to obtain Letermovir in a pure, chemically stable, and amorphous state to b) the provision of an adequate process for tablet/capsule manufacturing of amorphous Letermovir that provides for sufficient dissolution properties to be implemented in IR tablet/capsule dosage forms, i.e. >50% dissolution of Letermovir within 30 minutes.

The present invention, surprisingly und unexpectedly, provides for chemically stable, orally administrable solid pharmaceutical formulations of Letermovir or pharmaceutically acceptable salts, solvates or hydrates thereof characterized by dissolution of amorphous Letermovir in granulation formulation of >50% in 30 minutes.

Further, the present invention, surprisingly und unexpectedly, provides for chemically stable, orally administrable solid pharmaceutical formulations of Letermovir or pharmaceutically acceptable salts, solvates or hydrates thereof characterized by absolute bioavailability (F) of amorphous API Letermovir in granulation formulation of 30 to 95%, preferably 50 to 95%, more preferably 60 to 95%.

In another aspect the present invention, surprisingly und unexpectedly, provides for chemically stable, orally administrable solid pharmaceutical formulations of Letermovir or pharmaceutically acceptable salts, solvates or hydrates thereof characterized by absolute bioavailability (F) of amorphous API Letermovir in granulation formulation of >30%, preferably >40%, more preferably >50%, even more preferably >70%, even more preferred >80%, and most preferred >90%.

Chemical stability is crucial for a pharmaceutical agent to maintain its activity also in forms of applicable dosage forms such as a tablet or capsule for oral use. The one skilled in the art is aware that chemical stability of an API is inter alia depending on its isolation-process besides the composition of the formulation itself, its mixture, its method of manufacture and by the storage conditions itself. In this regard, it is common knowledge that impurities may degrade from an API, such as Letermovir due to e.g. an increase in correlation to storage temperature, storage relative humidity and the duration of storage.

Accordingly, in a first major aspect of the invention Letermovir is isolated out of a solution in an organic solvent in sufficient yield and purity and Letermovir remains stabilized in its amorphous state having conserved physicochemical properties in order to enable an oral tablet/capsule formulation that provides sufficient dissolution characteristics, i.e. >50% dissolution of amorphous Letermovir in 30 minutes.

Pursuant to the invention, in the final chemical synthesis step, Letermovir is prepared by saponification of the corresponding methyl ester, which was used for the separation of both enantiomers by crystallization using (2S,3S)-(+)-Di-O-4-toluoyl-D-tartaric acid. The chiral acid was removed by extraction with aqueous bicarbonate from a methyl-tert-butyl-ether (hereinafter MTBE) solution, and the methyl ester of Letermovir was saponified using aqueous sodium hydroxide in a biphasic mixture.

After saponification, the zwitterionic form could be extracted to MTBE at neutral pH. Finally, a solvent switch to acetone was performed and the amorphous API Letermovir could be isolated by either use of i) a roller dryer, or ii) by precipitation of an acetonic or acetonitrile solution of the amorphous API Letermovir into an excess of stirred water with subsequent drying at elevated temperature of 40-80° C. in a conical dryer.

Alternatively, the precipitation can be forced by adding water as anti-solvent to an acetonitrile or acetone solution of the amorphous API Letermovir. This process leads to sticky material, which has to be processed further to receive solid amorphous API Letermovir, which can be isolated by filtration.

Due to the above isolation methods, Letermovir can be isolated in the amorphous state, in chemical and chiral purity with acceptable limits of residual solvents, exhibiting physicochemical properties, which are appropriate for galenic formulation without further steps such as milling, or micronization.

Said physicochemical properties include a specific surface area of amorphous Letermovir obtained in accordance with the invention of at least 1 $m^2/g$, when the isolated Letermovir is subjected to a Brunauer-Emmett-Teller (BET) specific surface area (SSA) analysis while applying the following exemplary conditions:
Principle: Nitrogen adsorption at 77 K; method according to Brunauer, Emmett and Teller (BET)
Method: volumetric method (method II) according to USP <846>
Instrument: Tristar 3000/VacPrep 061 (Micromeritics)
Sample mass: approximately 1.5-2.5 g
Sample preparation: degassing for 2 h at 40° C. under vacuum (final vacuum <2.7 Pa)
Pressure range p/p0: 0.05-0.15 (3 data points).

Said physicochemical properties also include a particle size distribution (PSD) median value of not more than 10 μm, when the isolated Letermovir of the invention is subjected to a particle size distribution analysis while applying the following exemplary conditions:
Device: Mastersizer 2000 with dry dispersion
Modus: Fraunhofer; weight-in quantity: 0.3-0.4 g
Measurement time: 20 seconds
Background time: 6 seconds
Obscuration limits: 0.5 to 6%
Sample tray: micro volume; small sieve with balls
Feed rate: 45-55%
Dispersive pressure: 2.5 bar Four independent analyses are to be performed and the results have to be averaged.

Said physicochemical properties also include a pharmaceutically acceptable toxic impurity content of isolated Letermovir pursuant to the invention, namely:
i) an impurity content of mesityl oxide of </=31 ppm, when determined by static headspace gas chromatography as set out in detail in the below specific embodiment bearing the number
and/or
ii) an impurity content of 3-methoxyaniline of <20 ppm, preferably <15 ppm, more preferably <10 ppm, even more preferably <5 ppm, most preferred <1.5 ppm, when determined by gas chromatography having the following operating conditions:

| Instrument | Gas Chromatograph, e.g. Agilent 6890 |
|---|---|
| Column | DB-1 |
| | 60 m length, 0.25 mm internal diameter, 1 μm film thickness |
| Carrier gas, flow rate | Nitrogen, 1.7 mL/min, constant flow |
| Split ratio | 1:5 |
| Injector temperature | 150° C. |

| Oven temperature program | |
|---|---|
| Starting temperature | 70° C. |
| Holding time | 5 min |
| 1. Heating rate | 8K/min |
| 1. Final temperature | 120° C. |
| Holding time | 22 min |
| 2. Heating rate | 25K/min |
| 2. Final temperature | 300° C. |
| Holding time | 2 min |
| Analysis time | 42.45 min |
| Injection volume | 5 μl |
| FID: | |
| Temperature | 300° C. |
| Burning gases | Hydrogen: 40 mL/min; Air: 450 mL/min |
| Make-up Gas ($N_2$) | 25 mL/min |

Purge Run

| Carrier gas, flow rate | Nitrogen: 2.5 mL/min, constant flow |
|---|---|
| Split ratio | 1:5 |
| Injector temperature | 300° C. |
| Oven temperature program | |
| Starting temperature | 300° C. |
| Holding time | 15 min |
| Analysis time | 15 min |
| Injection volume | 5 μl. |

With the above context, the person skilled in the art is aware that the specific surface area of a powder like amorphous Letermovir increases as the particle size decreases. Accordingly, the surface of the active pharmaceutical ingredient Letermovir increases, which improves its dissolution and resorption profile when administered orally in solid dosage forms.

It is a surprising and unexpected finding of the invention that by the isolation methods as disclosed herein amorphous Letermovir can be obtained with a median particle size distribution of not more than 10 μm and/or a specific surface area of at least 1 $m^2/g$. In addition, the amorphous Letermovir obtained by the methods of the invention exhibits a high degree of purity, which makes it pharmaceutically acceptable to be readily formulated in solid oral dosage forms.

Following this, the inventors have found galenic formulations for the isolated Letermovir in the amorphous state that preserve said amorphous state without affecting its pharmaceutical activity and dissolution properties.

Accordingly, in a second major aspect of the invention, surprisingly and unexpectedly, the inventors have found chemically stable galenic formulations of amorphous Letermovir having dissolution properties of amorphous Letermovir in granulation formulation of >50% within 30 minutes.

With the context of the second major aspect of the present invention, surprisingly and unexpectedly, the inventors have found solid pharmaceutical formulations of Letermovir in the amorphous state exhibiting an absolute bioavailability (F) of 30 to 95%, preferably 50 to 95%, more preferably 60 to 95%.

Thus, the present invention combines the advantages of the metastable amorphous state of Letermovir, i.e. improved dissolution properties, with appropriate galenic formulations to preserve the amorphous state, and thus to provide for orally administrable solid dosage forms such as tablets or capsules. Moreover, the present invention exploits the lipophilicity of Letermovir in the amorphous state, so to obtain solid pharmaceutical formulations of Letermovir exhibiting an absolute bioavailability (F) of amorphous API Letermovir in granulation formulation of >30%, preferably >40%, more preferably >50%, even more preferably >70%, even more preferred >80%, and most preferred >90%.

Despite improvements in regard to dissolution properties, also the lipophilicity of Letermovir in the amorphous state—that is preserved by the isolation techniques and the manufacturing processes according to the invention—improves the bioavailability properties of an amorphous API Letermovir, which is known to the person skilled in the art.

Moreover, it is commonly known that the amorphous state is a metastable state, which results in a thermodynamic drive towards crystallization. In cases where a predominantly crystalline drug is converted to an amorphous state in order to enhance solubility and dissolution characteristics, it is common practice to prepare for instance a solid dispersion (or melt extrusion) of said drug using pharmaceutically acceptable polymers in order to stabilize the drug-polymer aggregate against crystallization.

However, due to the isolation techniques according to the first major aspect of the invention long-term stable solid pharmaceutical formulations of the amorphous Letermovir are provided without processing as a solid dispersion or melt extrusion. In this regard, the person skilled in the art is aware that the isolation of amorphous Letermovir in high quality is not a trivial exercise.

Isolating Letermovir by Using a Roller Dryer

The inventors have found that the process of roller drying for isolating Letermovir is adequate.

According to the invention, the process starts by
using a solution of Letermovir in acetone, applied as a very thin film on a heated rotating drum (40-60° C., preferably 60° C.), which is installed in a vacuum chamber having pressure of approximately 200 mbar,
the Letermovir is then removed from the drum using a scraping tool.

This process is limited in operational capacity and delivers Letermovir in the amorphous state, which has to undergo a final drying process
in order to fulfill the ICH requirements for residual solvents.
Isolating Letermovir Via Precipitation from Acetonitrile or Acetone into Excess Water The inventors further have found that Letermovir can be isolated in the amorphous state when precipitated from acetonitrile or acetone into excess water.

Therefore, in another aspect the present invention provides for a precipitation process for isolating amorphous Letermovir, characterized by precipitation from the water-miscible solvents acetonitrile or acetone into excess of stirred water. Following isolation via filtration or centrifugation. Subsequently, optionally a drying step in vacuo follows.

Following the stated above, the inventors found precipitation, filtration and drying in vacuo at elevated temperature of 40-80° C. to be adequate for isolation of amorphous Letermovir in excellent purity and with adequate physicochemical properties, particularly in terms of particle size distribution and specific surfaces area, which allows being further formulated into a tablet.

Influence of Solvents on Isolation of Letermovir

The inventors further have found that isolating Letermovir generally is solvent-dependent and thus specific and adequate solvents are needed to obtain Letermovir in a pure and chemically stable amorphous state.

During chemical development and optimization studies to obtain amorphous Letermovir in pharmaceutical grade the following water-miscible solvents were investigated: ethanol, tetrahydrofurane (THF), methyl ethyl ketone (MEK, 2-butanone), methanol and acetonitrile.

The inventors have found ethanol, THF and MEK to be not suitable as solvents for obtaining amorphous Letermovir in pharmaceutical grade either for quality reasons (impurities, residual solvents) or for the process of precipitation and precipitation itself.

Therefore, in another aspect of the present invention ethanol, THF and MEK are particularly disclaimed for precipitation and precipitation of Letermovir out of an organic solution, preferably an acetone solution.

In another aspect, the inventors found methanol to be disadvantageous for isolating Letermovir and to obtain an amorphous API in pharmaceutical grade since potential side reactions as re-esterification can occur under stress conditions, thus limiting scale-up of such an isolation process.

By contrast, the inventors have found against expectation that only acetonitrile and acetone provide for sufficient precipitation properties to obtain Letermovir in an amorphous state and in pharmaceutical grade. The thus obtained Letermovir exhibits sufficient purity and yield, as well as suitable physicochemical properties and thus can be directly used for the preparation of galenic formulations to be implemented in orally applicable tablet/capsule granulations.

Therefore, in another aspect of the invention acetonitrile and acetone are preferred as water-miscible solvents to be applied for precipitation of amorphous Letermovir. Acetone is even more preferred as the solvent with lower toxicity in view of the residual solvent limits required by the current ICH guidelines.

Thus, in another aspect of the invention acetone is the most preferred organic solvent to be applied for precipitation of amorphous Letermovir.

Furthermore, in accordance with the invention the residual solvents (acetonitrile, acetone, water) can effectively be removed in vacuo at elevated temperature (40-80° C.) without loss of purity or change of physicochemical properties in regard to the amorphous state, particle size distribution and the specific surface area.

In another aspect of the invention the isolated amorphous Letermovir has a content of acetone below 5000 ppm (pursuant to ICH guidelines), and a content of water <2% (internal limit).

To the second major aspect of the invention:
Manufacturing of Tablets/Capsules

Subject matter of the present invention are also manufacturing processes based on dry granulation and wet granulation (also known as high shear or top spray granulation) to obtain IR film coated tablets/capsules containing the isolated Letermovir in the amorphous state in different dose strengths. The inventors further have developed dry granulations to obtain IR film coated tablets containing the isolated Letermovir in the amorphous state in different dose strengths.

In accordance with the invention a dry granulation process can be conducted on a tablet press (slugging) or by using a roller compactor.

Therefore, another aspect of the instant invention is the provision of dry granulations of the isolated Letermovir in the amorphous state that can be obtained by a tablet press or by using a roller compactor.

Another underlying problem in regard to Letermovir as isolated amorphous API that is to be further processed in a granulation is the drying process itself.

In case the amorphous agent Letermovir dries on surface, a surrounding layer develops that impairs further drying.

Such behavior of an amorphous API for oral pharmaceutical formulations cannot be handled by classical drying techniques of the pharmaceutical industry and in addition comprises inherent scale-up limitations.

In accordance with the invention for dry and wet granulations of Letermovir in the amorphous state, polymers are used as binders, which are hydrophilic in nature and thus have beneficial effects to the dissolution properties of Letermovir, as it is a hydrophobic but lipophilic solid.

Therefore, in another aspect of the present invention the polymers used are selected from the group comprising but not limited to hydroxyl propyl methylcellulose (also known as hypromellose or HPMC), povidone (also known as polyvinyl pyrrolidone, polyvidone or PVP), starch (including pregelatinised starch) are used as binders in the granulation formulations pursuant to the invention.

Granulation Process/Wet and Dry Granulation

The inventors found that in case of wet granulation after mixing the solid fraction of amorphous Letermovir with ethanol, the resulting product was extremely wet and not reproducible; irrespective of the ethanol content.

Therefore, in a further aspect of the invention alcohols, in particular methanol and ethanol as processing agents are disclaimed for wet granulations of Letermovir in the amorphous state.

Therefore, in another aspect of the present invention acetone as processing agent for wet granulations of Letermovir in the amorphous state is disclaimed.

Thus, in a specific aspect of the invention also mixtures of ethanol and acetone as processing agents are disclaimed for wet granulations of Letermovir in the amorphous state.

To overcome the above hurdles the inventors have found that replacement of organic solvents with purified water led to an improved processing agent for wet granulations of the isolated amorphous Letermovir.

Thus, in one aspect of the invention purified water is a suitable processing agent for wet granulations of Letermovir in the amorphous state.

The inventors also found that the amorphous Letermovir isolated by roller-drying can be processed by wet granulation.

From a technical point of view, however, a dry granulation of isolated, amorphous Letermovir is preferred since no additional drying is required, which may also affect the physicochemical properties and stability of Letermovir.

Therefore, in another aspect of the invention the herein described solid pharmaceutical formulations contain amorphous Letermovir isolated by roller dryer, which is further processed by dry granulations thereof.

However, throughout the specification the API Letermovir in the amorphous state obtained by precipitation is preferred for further processing within the context of the invention.

In particular, the inventors have found that precipitated Letermovir shows beneficial properties to obtain homogenous mixtures thereof during the drying process accompanied by compaction for tabletting.

Therefore, in another aspect of the invention the herein described pharmaceutical dry granulations contain precipitated Letermovir.

Galenic formulations of roller dried and precipitated Letermovir

The person skilled in the art is aware that the isolation process of amorphous compounds itself influences the later tabletting properties during manufacture.

In the following, some parameters may slightly differ from the solid pharmaceutical formulations as described herein. However, a person skilled in the art knows such variations. Thus, a person skilled in the art understands that the following aspects are merely preferred aspects; however, the invention shall not be limited to such specific aspects.

In addition to the isolated Letermovir, which is in the amorphous state, the solid pharmaceutical formulations of the present invention contain one or more pharmaceutically acceptable ingredient(s) referred to as excipients. Common excipients include inter alia fillers, diluents, binders, lubricants, glidants, disintegrants, solvents, film formers, plasticizers, pigments, and antioxidant agents. All excipients as part of the present invention are either synthetic or plant origin, they are not derived from animal or human origin.

All the listed excipients that are potentially used in the manufacture of the herein provided solid pharmaceutical formulations of the amorphous API Letermovir are well known and widely used in the manufacture of pharmaceutical dosage forms (e.g. compressed tablets or capsules) using conventional pharmaceutical processes including granulation and compaction.

In another aspect of the present invention the solid pharmaceutical formulations of the present invention comprise one or more excipient(s) or a combination thereof selected from the group comprising microcrystalline cellulose, copovidone, croscarmellose sodium, colloidal anhydrous silica, magnesium stearate, povidone (also known as polyvinyl pyrrolidone, polyvidone or PVP), lactose, sucrose, mannitol, starch (including pregelatinised starch), talc, hydroxylpropyl cellulose, hydroxyl propyl methylcellulose (also known as hypromellose or HPMC), sodium starch glycolate, calcium hydrogenphosphate dihydrate (also known as dibasic calcium phosphate), triethyl citrate, methacrylic acid—methyl methacrylate copolymers, polyvinyl alcohol, magnesium stearate, macrogol, poly(vinylalcohol) grafted copolymer, polyvinyl acetate, methacrylic acid/ethyl acrylate copolymers.

In a preferred aspect the solid pharmaceutical formulations comprise Letermovir in the amorphous state as API with an amount of 20.0% to 70.0% (w/w), povidone with an amount of 1.0% to 30.0% (w/w), croscarmellose sodium with an amount of 1.0% to 30.0% (w/w), microcrystalline cellulose with an amount of 10.0% to 90.0% (w/w), colloidal anhydrous silica with an amount of 0.1% to 10.0% (w/w), and magnesium stearate with an amount of 0.01% to 10.0% (w/w).

In an especially preferred aspect the solid pharmaceutical formulations comprise Letermovir in the amorphous state as API with an amount of 30.0% to 50.0% (w/w), povidone with an amount of 2.0% to 10.0% (w/w), croscarmellose sodium with an amount of 2.0% to 10.0% (w/w), microcrystalline cellulose with an amount of 20.0% to 70.0% (w/w), colloidal anhydrous silica with an amount of 0.5% to 5.0% (w/w) and magnesium stearate with 0.1% to 5.0% (w/w).

Further, in another aspect of the invention the solid pharmaceutical formulations comprising Letermovir in the amorphous state are obtainable by granulation, preferably wet granulation.

In another aspect of the invention the solid pharmaceutical formulations comprising Letermovir in the amorphous state are obtainable by roller compaction/dry granulation.

In another aspect of the invention the solid pharmaceutical formulations comprising Letermovir in the amorphous state are obtainable by direct compression.

Precipitated amorphous Letermovir prepared by dry granulation represents a preferred embodiment of the present invention.

In particular, the inventors have found that a granulation with purified water/povidone solution was possible. The corresponding dissolution data revealed a dissolution of Letermovir of >50% within 30 minutes.

Therefore, in another aspect of the invention a solid pharmaceutical formulation is provided of Letermovir in the amorphous state obtained by roller-drying that is further processed with a purified water/povidone mixture as processing agent for wet granulation, having a dissolution of >50% within 30 minutes, preferably >60% within 30 minutes, more preferably >70% within 30 minutes, even more preferably >80% within 30 minutes, most preferred >90% within 30 minutes.

In another aspect of the invention a solid pharmaceutical formulation is provided of Letermovir in the amorphous state obtained by precipitation and further processed with a purified water/povidone mixture as processing agent for wet granulation, having a dissolution of >50% within 30 minutes, preferably >60% within 30 minutes, more preferably >70% within 30 minutes, even more preferably >80% within 30 minutes, most preferred >90% within 30 minutes.

In addition, the inventors have found that the dissolution of solid pharmaceutical formulations of precipitated Letermovir in the amorphous state that is further prepared by dry granulation is enhanced by the addition of disintegrating agents.

In particular, increased croscarmellose sodium as disintegrating agent, being raised from conventional 3% to 5%, improved the dissolution of amorphous Letermovir in an experimental tablet formulation for oral administration, and thereby enabled dissolution of >50% within 30 minutes, preferably >60% within 30 minutes, more preferably >70% within 30 minutes, even more preferably >80% within 30 minutes, most preferred >90% within 30 minutes.

Thus, in another aspect of the invention the solid pharmaceutical formulations of the amorphous Letermovir that contain croscarmellose sodium with at least 4%, preferably at least 5% in the solid pharmaceutical formulation exhibit dissolution of >50% within 30 minutes, preferably >60% within 30 minutes, more preferably >70% within 30 minutes, even more preferably >80% within 30 minutes, most preferred >90% within 30 minutes.

Accordingly, due to galenic reasons known to the person skilled in the art, the filler/binder microcrystalline cellulose have to be decreased in ratio to accommodate the increased croscarmellose sodium.

In another aspect of the invention the solid pharmaceutical formulations of the instant invention contain Letermovir in the amorphous state in an amount of at least 5%, preferably at least 15%, more preferably at least 30%, even more preferably at least 40%.

In general the inventors have found the amorphous Letermovir isolated by roller drying to be more suitable for processing using wet granulation and the precipitated amorphous Letermovir is more suitable for processing using dry granulation.

In another aspect of the invention the isolated amorphous Letermovir is contained in the solid pharmaceutical formulations for oral administration in the amount of 20 to 500 mg, preferably in the amount of 120 to 280 mg, most preferred in the amount of 240 mg or greater than 240 mg.

Further, in another aspect of the invention the isolated amorphous Letermovir is contained in the solid pharmaceutical formulations for oral administration in the amount of 20 to 400 mg, preferably in the amount of 120 to 280 mg, most preferred in the amount of 240 mg or greater than 240 mg.

In another aspect, subject matter of the invention are film-coated tablets containing the amorphous Letermovir in different dose strengths, i.e. 5 mg, or 20 mg, or 30 mg, or 60 mg, or 120 mg, or 240 mg of Letermovir, or >240 mg of Letermovir. Said distinct dose strengths should be not understood as limiting dose strengths. Any other dose strength reasonably administrable to a subject is also comprised by the scope of the present invention.

Method for Testing Dissolution

Throughout the specification the respective dissolution data are based on dissolution testing using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 15, 30, and 45 minutes as follows:

HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention time: 1.3 minutes
Column temperature: 40° C.
Injection volume: 20 μL
Flow rate: 1.5 ml/min
Mobile phase: Buffer pH 4.0/Acetonitrile; 55/45 v/v Long-term Stability Further subject matter of the present invention is long-term stable galenic formulations of amorphous Letermovir for oral administration. By the galenic formulations of the invention the precipitated amorphous Letermovir material exhibits physical and chemical stability during storage at 25° C. and 60% relative humidity for at least 36 months.

Therefore, in a third major aspect of the present invention the isolated amorphous Letermovir is physically and chemically stable in the herein provided galenic formulations for at least 36 months of storage at 25° C. and 60% relative humidity.

Oral Administration for Use in Methods of Treating Viral Infections

In a fourth major aspect of the present invention the herein provided galenic formulations containing amorphous Letermovir are intended for the manufacture of medicaments to be administered orally to a subject for prophylaxis or in a method of treatment of viral infections. Specific indications to be addressed by the herein provided solid pharmaceutical formulations containing the amorphous API Letermovir are selected from the group comprising HCMV infections in a subject, particularly HCMV infections in a subject having acquired immune deficiency syndrome (AIDS), HCMV-pneumonitis, HCMV-encephalitis, as well as gastrointestinal and systemic HCMV infection, HCMV infections in newborn and children, acute HCMV infection of pregnant women, HCMV infection in immunosuppressed cancer patients, and HCMV-positive cancer patients to address HCMV-mediated tumor progression (cf. J. Cinatl, et al., *FEMS Microbiology Reviews* 2004, 28, 59-77).

In another aspect of the invention the herein provided solid pharmaceutical formulations containing the amorphous API Letermovir are intended for the manufacture of medicaments to be administered orally to a subject for prophylaxis or in a method of treatment of diseases caused by virals of the group Herpesviridae.

In another aspect of the invention the herein provided solid pharmaceutical formulations containing the amorphous API Letermovir are intended to be used in combination with other antiviral active ingredients such as Valganciclovir, Ganciclovir, Valacyclovir, Acyclovir, Foscarnet, Cidofovir and derivatives thereof in a method of treatment of viral infections, in particular HCMV infections.

Further subject matter of the present invention is the use of the herein provided solid pharmaceutical formulations containing the amorphous API Letermovir for prophylaxis or in a method of treatment of viral infections. Specific indications for said use of the herein provided solid pharmaceutical formulations containing the amorphous API Letermovir are selected from the group comprising HCMV infections in a subject, particularly HCMV infections in a subject having AIDS, HCMV-pneumonitis, HCMV-encephalitis, as well as gastrointestinal and systemic HCMV infection, HCMV infections in newborn and children, acute HCMV infection of pregnant women, HCMV infection in immuno-suppressed cancer patients, HCMV-positive cancer patients to address HCMV-mediated tumor progression (cf. J. Cinatl, et al., *FEMS Microbiology Reviews* 2004, 28, 59-77).

Another embodiment of the present invention is the use of the herein provided solid pharmaceutical formulations containing the amorphous API Letermovir for prophylaxis or in a method of treatment of diseases caused by virals of the group Herpesviridae.

In context with the stated above, particularly preferred subject matter of the present invention is provided by the following consecutively numbered and inter-related embodiments:

1. Letermovir according to Formula (I),

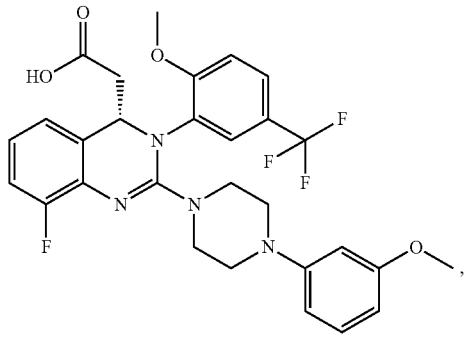

Formula (I)

which is in the amorphous state and suitable for use in solid oral dosage forms, wherein said Letermovir is characterized by
 i) a specific surface area of at least 1 m²/g when being subjected to a BET specific surface area analysis and/or
 ii) a particle size distribution median value of not more than 10 μm when being subjected to a particle size distribution analysis.

2. Letermovir according to embodiment 1, wherein under i) said BET specific surface area analysis is characterized by the following parameter:
Principle: Nitrogen adsorption at 77 K; method according to Brunauer, Emmett and Teller
Method: volumetric method; method II according to USP <846>
Instrument: Tristar 3000/VacPrep 061 (Micromeritics)
Sample mass: approximately 1.5-2.5 g
Sample preparation: degassing for 2 h at 40° C. under vacuum; final vacuum <2.7 Pa
Pressure range p/p0: 0.05-0.15; 3 data points.

3. Letermovir according to embodiment 1 or embodiment 2, wherein under item ii) said particle size distribution analysis is characterized by the following parameter:
Device: Mastersizer 2000 with dry dispersion
Modus: Fraunhofer; weight-in quantity; 0.3-0.4 g
Measurement time: 20 seconds
Background time: 6 seconds
Obscuration limits: 0.5 to 6%
Sample tray: micro volume; small sieve with balls
Feed rate: 45-55%
Dispersive pressure: 2.5 bar;
whereby four independent analyses are performed and the results are averaged.

4. Letermovir according to any of the preceding embodiments, wherein said amorphous state is characterized by no detectable crystalline content/signal within the limit of detection of 2%, when said Letermovir is determined by any of the three standard XRPD methods i), ii), or iii):
 wherein in i) A Letermovir powder sample is prepared on a rotating sample holder with an effective surface area of 1.9 mm (in diameter); powder diffraction patterns are recorded using a Bruker D8 Advance powder diffractometer equipped with a LynxEye PSD detector and Ni β-filter using CuKα radiation operated at 40 kV and 30 mA; and the measurement is performed using a step size of 0.06° with a step time of 0.5 s;
 wherein in ii) A Siemens Powder Diffractometer D5000 equipped with a secondary graphite monochromator using CuKα radiation operated at 40 kV and 30 mA is used; the effective surface area amounts to 6×10 mm; and the measurement is performed using a step size of 0.02° with a step time of 2 s;
 wherein in iii) A Seifert X-ray tube DX-Cu8*0,4-S equipped with a Germanium (111) Monochromator 616.2 and an Imaging Plate Guinier Camera G670 from Huber using CuKα radiation operated at 40 kV and 30 mA at a scan range of 0°<2Θ<100° and a step width of Δ(2→)=0.005° are used.

5. Letermovir according to any of the preceding embodiments, wherein said Letermovir in the amorphous state is zwitterionic having a pI of 5.55.

6. Letermovir according to any of the preceding embodiments, obtainable by the following process:
 a) providing an organic solution of Letermovir and either
 b1) isolating said Letermovir by roller-drying of said organic solution in a volatile organic solvent, in particular acetone, at a temperature of 30° C. to 60° C., particularly 40° C. to 50° C., and subsequently drying the amorphous Letermovir obtained, or
 b2) isolating said Letermovir by precipitation of the amorphous Letermovir from water miscible solvents, in particular acetone or acetonitrile, into excess water as anti-solvent, and subsequently filtrating or centrifuging the Letermovir obtained.

7. Letermovir according to embodiment 6, wherein the process according to step b2) has a final drying step.

8. Letermovir according to embodiment 6 or 7, wherein the Letermovir obtained in step b1) or b2) is processed by wet granulation.

9. Letermovir according to embodiment 6 or 7, wherein the Letermovir obtained in step b1) or b2) is processed by dry granulation.

10. Letermovir according to any of the embodiments 6 to 9, wherein said Letermovir in the amorphous state is not isolated by spray drying or evaporation of a solution of Letermovir in an organic solvent.

11. Letermovir according to any of the embodiments 6 to 10, wherein under step b2) said Letermovir in the amorphous state is not isolated by precipitation using alcohols, particularly methanol, or ethanol, or using THF or MEK.

12. Letermovir according to any of the preceding embodiments, wherein said Letermovir in the amorphous state has a content of acetone below 5000 ppm or a content of acetonitrile below 410 ppm, and a content of water <2.0%, when said acetone or acetonitrile content is determined by static headspace gas chromatography, having the following operating conditions:

| | |
|---|---|
| Apparatus | Gas Chromatograph, e.g. Agilent 6890 |
| Column | DB-WAXetr: 30 m length, 0.32 mm inner diameter, 1 μm thickness of film |
| Carrier gas, flow rate | Nitrogen, 0.9 mL/min (constant flow) 120 kPa vial pressure at the headspace sampler |
| Injector temperature | 250° C. |
| Split flow rate | 4.5 mL/min |
| Detector/temperature | FID/250° C. |
| Burning gases: | |
| Hydrogen | 40 mL/min |
| Air | 450 mL/min |
| Make-up gas ($N_2$) | 25 mL/min |
| Oven temperature program: | |
| Starting temperature | 40° C. |
| Holding time | 8 min |
| Heating rate | 20K/min |
| Final temperature | 70° C. |
| Holding time | 3 min |
| Cooling rate | 20K/min |
| Final temperature | 50° C. |
| Holding time | 3 min |
| Heating rate | 15K/min |
| Final temperature | 220° C. |
| Holding time | 3 min |
| Period of analysis | 30.8 min |
| Equipment | Headspace Autosampler, e.g. G1888 |
| Sample temperature | 100° C. |
| Needle temperature | 220° C. |
| Transfer temperature | 230° C. |
| GC cycle time | 40 min |
| Equilibration time | 30 min |
| Equilibration time before the 1st run | 1 min |
| Number of extractions | 1 |
| Shaking during equilibration time | 1 (slow) |
| Valve times | Pressurization time 0.25 min |
| | Loop fill time 0.20 min |
| | Loop equilibration time 0.05 min |
| | Inject time 0.50 min |
| Injections volume | 1 mL; | and when said water content is determined by PhEur 2.5.12.

13. A method for obtaining the Letermovir according to any of the embodiments 1 to 5 comprising the following steps:
   a) providing an organic solution of Letermovir and either
   b1) isolating said Letermovir by roller-drying of said organic solution in a volatile organic solvent, in particular acetone, at a temperature of 30° C. to 60° C., particularly 40° C. to 50° C., and subsequently drying the amorphous Letermovir obtained, or
   b2) isolating said Letermovir by precipitation of the amorphous Letermovir from water miscible solvents, in particular acetone or acetonitrile, into excess water as anti-solvent, and subsequently filtrating or centrifuging the Letermovir obtained.

14. The method according to embodiment 13 further comprising a final drying step after step b2).

15. The method according to embodiment 13 or 14 further comprising the step of processing the Letermovir obtained in step b1) or b2) by wet granulation.

16. The method according to embodiment 13 or 14 further comprising the step of processing the Letermovir obtained in step b1) or b2) by dry granulation.

17. The method according to any of the embodiments 13 to 16, wherein the precipitation in step b2) is not conducted while using alcohols or using THF or MEK.

18. Solid pharmaceutical formulation comprising Letermovir in the amorphous state, wherein said solid pharmaceutical formulation is orally administrable.

19. Solid pharmaceutical formulation according to embodiment 18, comprising Letermovir in the amorphous state as defined in any of the embodiments 1 to 12.

20. Solid pharmaceutical formulation according to embodiment 18, comprising the Letermovir obtained from the method as defined in any of the embodiments 13 to 17.

21. Solid pharmaceutical formulation according to embodiment 20, wherein the Letermovir is isolated according to step b1) of embodiment 13 and processed according to embodiment 15.

22. Solid pharmaceutical formulation according to embodiment 20, wherein the Letermovir is isolated according to step b2) of embodiment 13 and processed according to embodiment 16.

23. Solid pharmaceutical formulation according to any of the embodiments 18 to 20, which is effective to achieve an absolute bioavailability of 70%±30% of Letermovir when administered orally in said formulation comprising at least 5 mg of Letermovir in the amorphous state.

24. Solid pharmaceutical formulation according to embodiment 23, which is effective to achieve an absolute bioavailability of 70%±30% of Letermovir when administered orally in said formulation comprising >240 mg of Letermovir in the amorphous state.

25. Solid pharmaceutical formulation according to embodiment 23 or 24, further comprising povidone, croscarmellose sodium, microcrystalline cellulose, colloidal anhydrous silica and magnesium stearate.

26. Solid pharmaceutical formulation according to embodiment 25, wherein said Letermovir in the amorphous state is comprised in an amount of 30.0% to 50.0% (w/w), said povidone is comprised in an amount of 2.0% to 10.0% (w/w), said croscarmellose sodium is comprised in an amount of 2.0% to 10.0% (w/w), said microcrystalline cellulose is comprised in an amount of 20.0% to 70.0% (w/w), said colloidal anhydrous silica is comprised in an amount of 0.5% to 5.0% (w/w), and said magnesium stearate is comprised in an amount of 0.1% to 5.0% (w/w).

27. Solid pharmaceutical formulation according to the embodiments 25 or 26, comprising croscarmellose sodium as disintegrating agent in an amount of at least 4.0% (w/w).

28. Solid pharmaceutical formulation according to embodiment 27, comprising croscarmellose sodium as disintegrating agent in an amount of at least 5.0% (w/w).

29. Solid pharmaceutical formulation according to any of the embodiments 18 to 28, wherein a solution of arginine, in particular a solution of L-arginine is not comprised in said pharmaceutical formulation.

30. Solid pharmaceutical formulation according to any of the embodiments 18 to 29, wherein Letermovir in the amorphous state is contained in a dose strength of 5 mg, or 20 mg, or 30 mg, or 60 mg, or 120 mg, or 240 mg, or >240 mg.

31. Solid pharmaceutical formulation according to any of the embodiments 18 to 30, wherein Letermovir in the amorphous state exhibits a dissolution of >50% within 30 minutes, preferably >60% within 30 minutes, more preferably >70% within 30 minutes, even more preferably >80% within 30 minutes, most preferred >90% within 30 minutes,
when tested for dissolution of Letermovir in the amorphous state using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 30 minutes as follows:
HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention Time: 1.3 minutes
Column temperature: 40° C.
Injection volume: 20 μL
Flow rate: 1.5 ml/min
Mobile phase: Buffer pH 4.0/Acetonitrile; 55/45 v/v.

32. Solid pharmaceutical formulation according to any of the embodiments 18 to 31, wherein said solid pharmaceutical formulation is an immediate release formulation, characterized in that not less than 85% amount of the Letermovir in the amorphous state is dissolved within 30 min using USP Apparatus I at 100 rpm or USP Apparatus II at 50 rpm in a volume of 900 ml or less of each of the following media:
  (1) acidic media, such as USP simulated gastric fluid without enzymes;
  (2) pH 4.5 buffer; and
  (3) pH 6.8 buffer or USP-simulated intestinal fluid without enzymes.

33. Solid pharmaceutical formulation according to any of the embodiments 18 to 32, wherein said Letermovir in the amorphous state exhibits a chemical stability of at least 36 months during storage at room temperature (25° C.) and (60%) relative humidity, when determined by gradient reverse phase HPLC as follows:
HPLC Operating Conditions:
Column: Intertsil ODS III 5 μm or equivalent
Solvent Acetonitrile/0.1 N HCl; 3+7 (v/v)
Eluent A: Water, pH 2.40; B: Acetonitrile
Detection wavelength: 235 nm
Column temperature: 40° C.
Injection volume: 15 μL
Flow rate: 1.0 ml/min
Run time: 30 minutes.

34. Solid pharmaceutical formulation according to any of embodiments 18 to 33 for use in a method for prophylaxis or method of treatment for diseases associated with the group of Herpesviridae, preferably associated with cytomegalovirus (CMV), even more preferably associated with human cytomegalovirus (HCMV).

35. Solid pharmaceutical formulation according to embodiment 34 for use in a method of prophylaxis or method of treatment for diseases selected from the group comprising HCMV infections in a subject, particularly HCMV infections in a subject having AIDS, HCMV-pneumonitis, HCMV-encephalitis, as well as gastrointestinal and systemic HCMV infection, HCMV infections in newborn and children, acute HCMV infection of pregnant women, HCMV infection in immuno-suppressed cancer patients, HCMV-positive cancer patients to address HCMV-mediated tumor progression.

In another aspect of the invention Letermovir in the amorphous state is long-term stable in terms of maintaining the amorphous state without processing as a solid dispersion or melt extrusion for at least 36 months of storage at 25° C. room temperature and 60% humidity.

In accordance with the invention the "volatile solvents" are selected from the group comprising methanol, ethanol, acetonitrile, dichloromethane, and MTBE.

In accordance with the invention the "anti-solvent" is water.

In accordance with the invention the "organic solvent" is selected from the group comprising acetonitrile, and acetone.

Definitions

The term "amorphous" in the context of the present invention for solid Letermovir denotes the characteristic that no long-range order of neighboring molecular units is present while their crystalline counterparts have well defined long-range order. Thus, amorphous Letermovir has the two characteristics; a) the mechanical, thermal, electrical, and chemical properties of Letermovir are independent of the direction of measurement in the substance (isotropy), and b) with increased temperature, Letermovir softens and enters the liquid state only gradually, this means there is no definite melting point in the amorphous state.

Accordingly, Letermovir is in the amorphous state when exhibiting no detectable crystalline content/signal attributable to the tested Letermovir when analyzed by an appropriate crystallographic method.

Accordingly, throughout the specification the expressions "amorphous, amorphous form, amorphous state" with the context of the present invention denotes material exhibiting no indication of crystallinity within the limit of detection of 2% by using standard XRPD methods and thus exhibits no detectable crystalline content/signal when analyzed by an appropriate crystallographic method. Typically X-ray powder diffraction (XRPD) is used to determine the crystalline content of the material in accordance with the invention. Three exemplary methods of analysis are described below, but not limited to:

a) The sample was prepared on a rotating sample holder with an effective surface area of 1.9 mm (in diameter). Powder diffraction patterns were recorded using a Bruker D8 Advance powder diffractometer equipped with LynxEye PSD detector and Ni β-filter using CuKα radiation operated at 40 kV and 30 mA. The measurement was performed using a step size of 0.06° with a step time of 0.5 s.

b) A Siemens Powder Diffractometer D5000 equipped with secondary graphite monochromator using CuKα radiation operated at 40 kV and 30 mA was used.

The effective surface area amounts to 6×10 mm. The measurement was performed using a step size of 0.02° with a step time of 2 s.

c) A Seifert X-ray tube DX-Cu8*0,4-S equipped with a Germanium (111) Monochromator 616.2 and a Imaging Plate Guinier Camera G670 from Huber using CuKα radiation operated at 40 kV and 30 mA at a scan range of 0°<2Θ<100° and a step width of Δ(2Θ)=0.005°.

"Isotropy" of properties is also characteristic of the polycrystal state. This, however, is characterized by a strictly defined fusion temperature, and this fact justifies separating it from the amorphous state of Letermovir. The structural difference between the amorphous and the crystal states is readily detectable on X-ray diagrams obtained by e.g. the above-described XRPD methods. Monochromatic X-rays scattered on crystals form a diffraction picture consisting of distinct peaks is not characteristic of the amorphous state.

As stated above, the characteristics of amorphous Letermovir result from the absence of long-range order. By contrast, such long-range order is present in crystals, which exhibit strict periodicity in all directions of one and the same structural element, i.e. atom, atom group, molecule, and so forth through hundreds and thousands of periods. At the same time, Letermovir in the amorphous state possesses short-range order.

In the context of the instant invention "short range order" denotes regularity in the position of neighboring particles of Letermovir, i.e. the order observed at distances comparable to the molecular dimensions when measured by electric-field gradient on a probe nucleus of Letermovir. With distance this agreement diminishes, and after 0.5-1 nanometer it disappears. Short-range order is also characteristic of liquids, but in the case of liquids there is an intensive exchange of positions between neighboring particles; however, this exchange is retarded with increase in viscosity of Letermovir. Viscosity of Letermovir in accordance with the invention may be determined by viscometers and/or rheometers known to the person skilled in the art.

The expressions "zwitterionic, zwitterionic properties, and zwitterion" in the context of the present invention for the API Letermovir means that a Letermovir molecule is a neutral molecule having a positive and a negative electrical charge at different locations within the same molecule. Accordingly, the API Letermovir has a charge, which changes with pH when measured in an electric field. Thus, Letermovir migrates in an electric field and the direction of migration depends upon the net charge possessed by the molecules. The net charge is influenced by the pH value. Letermovir has a fixed value of isoelectric point (pI) being the pH value at which the number of cations is equal to that of anions. At this point (pI=5.55) the net electric charge of Letermovir is always zero.

The terms "dissolution, dissolution properties" denote the process or the characteristic by which a solid, liquid or gas forms a solution in a solvent. For the dissolution of solids, the process of dissolution can be explained as the breakdown of the crystal lattice into individual ions, atoms or molecules and their transport into the solvent. Overall the free energy must be negative for net dissolution to occur.

Throughout the specification the expression "sufficient dissolution" with the context of the amorphous Letermovir in accordance with the invention denotes >50% dissolution in 30 minutes, preferably >60% dissolution in 30 minutes, more preferably >70% dissolution in 30 minutes, even more preferably >75% dissolution in 30 minutes, even more preferably >80% dissolution in 30 minutes, even more preferably >85% dissolution in 30 minutes, most preferred >90% dissolution in 30 minutes when tested for dissolution using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 15, 30, and 45 minutes as follows:

HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention Time: 1.3 minutes
Column temperature: 40° C.
Injection volume: 20 μL
Flow rate: 1.5 ml/min
Mobile phase: Buffer pH 4.0/Acetonitrile; 55/45 v/v By contrast, "solubility" is the property of a solid, liquid, or gaseous chemical substance called solute to dissolve in a solid, liquid, or gaseous solvent to form a homogeneous solution of the solute in the solvent. The solubility of a substance fundamentally depends on the used solvent as well as on temperature and pressure. The extent of the solubility of a substance in a specific solvent is measured as the saturation concentration, where adding more solute does not increase the concentration of the solution. Solubility is not to be confused with the ability to dissolve or liquefy a substance, because the solution might occur not only because of dissolution but also because of a chemical reaction. Solubility does not also depend on particle size or other kinetic factors; given enough time, even large particles will eventually dissolve.

The term "bioavailability" denotes in general a subcategory of absorption and is the fraction of an administered dose of Letermovir that reaches the systemic circulation, one of the principal pharmacokinetic properties of drugs. By definition, when a medication is administered intravenously, its bioavailability is 100%. However, when a medication is administered via other routes (such as orally), its bioavailability generally decreases (due to incomplete absorption and first-pass metabolism) or may vary from individual to individual. Bioavailability is one of the essential tools in pharmacokinetics, as bioavailability must be considered when calculating dosages for non-intravenous routes of administration.

With the context of the API amorphous Letermovir of the present invention, the expression "sufficient bioavailability" means that amorphous Letermovir in the solid pharmaceutical formulations of the invention exhibits an absolute bioavailability (F) of 30 to 95%, preferably 50 to 95%, more preferably 60 to 95%, when administered in oral dosage forms. In other words, the expression also means that the chemically stable, orally administrable solid pharmaceutical formulations of amorphous Letermovir or pharmaceutically acceptable salts, solvates or hydrates thereof are characterized by an absolute bioavailability (F) of the amorphous API Letermovir in granulation formulation of >30%, preferably >40%, more preferably >50%, even more preferably >70%, even more preferred >80%, and most preferred >90%.

The expression "immediate release or IR tablet formulation" with the context of the present invention generally denotes tablets and capsules that release the API Letermovir within a small period of time, typically less than 30 minutes. Specifically, said expression denotes the characteristics that not less than 85% of the Letermovir drug amount is dissolved within 30 min using USP Apparatus I at 100 rpm or USP Apparatus II at 50 rpm in a volume of 900 ml or less of each of the following media:
(1) acidic media, such as USP simulated gastric fluid without enzymes;
(2) pH 4.5 buffer; and
(3) pH 6.8 buffer or USP-simulated intestinal fluid without enzymes.

Otherwise, the Letermovir product is considered to be "slow dissolving".

Accordingly, the term "extended- or sustained release tablet formulation" with the context of the present invention denotes tablets and capsules that release the API Letermovir at a sustained and controlled release rate over a period of time. Typically extended-release tablets and capsules release their ingredient with time periods of 8 hours, 12 hours, 16 hours, and 24 hours when tested by USP Apparatus I at 100 rpm or USP Apparatus II as described above.

An "IR product, IR tablet/capsule dosage form" is characterized as rapidly dissolved if not less than 85% of the labeled drug amount is dissolved within 30 min using USP Apparatus I at 100 rpm or USP Apparatus II at 50 rpm in a volume of 900 ml or less of each of the following media:

(1) acidic media, such as USP simulated gastric fluid without enzymes;
(2) pH 4.5 buffer; and
(3) pH 6.8 buffer or USP-simulated intestinal fluid without enzymes.

Otherwise, the drug product is considered to be slow dissolving.

The term "pharmaceutical activity" of Letermovir denotes the antiviral activity against HCMV isolates of the respective individual, being in the range of $EC_{50}\pm SD$ of 0.0005 to 0.005±0.0001 to 0.001.

The term "chemically stable" within the context of the present invention denotes resistance to a purity of at least 97.0%, preferably above 97.0%, most preferably above 98.0%, most preferred above 99.0% of the API Letermovir in the provided solid pharmaceutical formulations. Alternatively "chemically stable" may also be characterized in that the maximal amount of degradation under usual storage conditions (5° C.-40° C., 40-80% relative humidity), impurities degraded from the API is less than 3.0% mass fraction of the initial total mass of API thereof when said formulation is measured at a certain time point by an appropriate HPLC method as for instance:

Gradient reverse phase HPLC assay, used to determine the drug product identification and degradation products
Operating Conditions:
Column: Intertsil ODS III 5 μm or equivalent
Solvent Acetonitrile/0.1 N HCl; 3+7 (v/v)
Eluent A: Water, pH 2.40; B: Acetonitrile
Detection wavelength: 235 nm
Column temperature: 40° C.
Injection volume: 15 μL
Flow rate: 1.0 ml/min
Run time: 30 minutes The term "physically stable" within the context of the present invention reflects no detectable crystalline content/signal attributable to the API when analyzed by an appropriate crystallographic method and in addition no significant change in particle size distribution and specific surface area.

The terms "pure/purified" in view of the API Letermovir characterizes the API in that it is not contaminated with
a) impurities from degradation or side products from reagents or synthetic process steps,
b) residual solvents or water exceeding a certain range, i.e. residual solvents according to current guidelines and <2% residual water in accordance with the instant invention.

Further said terms denote that no residual MTBE content is present. In addition said terms denote that the mesityl oxide content does not exceed 800 ppm when determined by Gradient reverse phase HPLC assay, used to determine the drug product identification and degradation products
Operating Conditions:
Column: Intertsil ODS III 5 μm or equivalent
Solvent Acetonitrile/0.1 N HCl; 3+7 (v/v)
Eluent A: Water, pH 2.40; B: Acetonitrile
Detection wavelength: 235 nm
Column temperature: 40° C.
Injection volume: 15 μL
Flow rate: 1.0 ml/min
Run time: 30 minutes.

With this context, the expression "pharmaceutically acceptable impurity contents" as regards the isolated amorphous Letermovir of the invention means that the amorphous Letermovir thus obtained is further characterized by a mesityl oxide content of <1=31 ppm, preferably of <1=27 ppm, even more preferably of <1=23 ppm, most preferred of <1=10 ppm, when determined by static headspace gas chromatography as set out in detail in the above specific embodiment bearing the number 12
and/or
a 3-methoxyaniline content of <20 ppm, preferably <15 ppm, more preferably <10 ppm, even more preferably <5 ppm, most preferred <1.5 ppm, when determined by gas chromatography having the following operating conditions:

| Instrument | Gas Chromatograph, e.g. Agilent 6890 |
|---|---|
| Column | DB-1 |
| | 60 m length, 0.25 mm internal diameter, 1 μm film thickness |
| Carrier gas, flow rate | Nitrogen, 1.7 mL/min, constant flow |
| Split ratio | 1:5 |
| Injector temperature | 150° C. |
| Oven temperature program | |
| Starting temperature | 70° C. |
| Holding time | 5 min |
| 1. Heating rate | 8K/min |
| 1. Final temperature | 120° C. |
| Holding time | 22 min |
| 2. Heating rate | 25K/min |
| 2. Final temperature | 300° C. |
| Holding time | 2 min |
| Analysis time | 42.45 min |
| Injection volume | 5 μl |
| FID: | |
| Temperature | 300° C. |
| Burning gases | Hydrogen: 40 mL/min; Air: 450 mL/min |
| Make-up Gas ($N_2$) | 25 mL/min |

Purge Run

| Carrier gas, flow rate | Nitrogen: 2.5 mL/min, constant flow |
|---|---|
| Split ratio | 1:5 |
| Injector temperature | 300° C. |
| Oven temperature program | |
| Starting temperature | 300° C. |
| Holding time | 15 min |
| Analysis time | 15 min |
| Injection volume | 5 μl | and/or that no residual MTBE content is present and/or that <2% residual water is present and/or that below 5000 ppm residual acetone is present and/or that below 410 ppm of residual acetonitrile is present, when determined by its respective methods as outlined above.

The term "metastable" with the context of amorphous Letermovir denotes a chemical state of temporary energy trap or a somewhat stable intermediate stage of a system the energy of which may be lost in discrete amounts.

The term "chiral purity" with the context of amorphous Letermovir denotes >99% present Letermovir in one enantiomeric form of the R/S system, when determined by Chiral HPLC assay:
Operating Conditions:
Column: Chiralpak AD-H, 5 μm; 250×4.6 mm
Mobile Phase: Mix 900 ml of n-heptane with 100 ml of 2-propanol and with 10 ml of diethyl amine
Isocratic: 50 min
Detection wavelength: UV detection 260 nm, BW+/−4 nm
Column temperature: 45° C.
Injection volume: 20 μL
Flow rate: 1.0 ml/min.

The expression "acceptable limits of residual solvents" denotes the amount of residual solvents being in accordance with the ICH guidelines.

The term "residual solvents" in terms of pharmaceuticals are defined here as organic volatile chemicals that are used or produced in the manufacture of drug substances or excipients, or in the preparation of drug products, as in the present case drugs substances based on Letermovir.

The solvents are not completely removed by practical manufacturing techniques. Appropriate selection of the solvents for the synthesis of drug substance based on toxicologically acceptable limits is crucial for pharmaceutical galenics. Since there is no therapeutic benefit from residual solvents, all residual solvents should be removed to the extent possible to meet product specifications, good manufacturing practices, or other quality-based requirements. Drug products should contain no higher levels of residual solvents than can be supported by safety data.

In accordance with the invention the term "highest dose strength" preferably denotes 240 mg to 480 mg Letermovir.

In accordance with the invention the term "highest dose strength" denotes 240 mg to 360 mg Letermovir.

The expression "long-term stable" with the context of the present invention denotes >99% purity of Letermovir for at least 24 months storage at 25° C. and 60% relative humidity when measured with HPLC.

The expressions "adequate physicochemical properties, physicochemical properties" with the context of amorphous Letermovir pursuant to the present invention denotes the characteristics Electrostatic behavior, particle size distribution and specific surface area being adequate for tableting processes Limited hygroscopicity to enable processing under production conditions not requiring controlled humidity equipment Chemical stability under storage and processing conditions of 25° C. and 60% relative humidity No tendency for uncontrolled crystallization when determined by suitable XRPD analysis.

Specifically, the expressions "adequate physicochemical properties, physicochemical properties" include a specific surface area of isolated amorphous Letermovir of at least 1 $m^2/g$ when the isolated Letermovir pursuant to the present invention is subjected to a BET specific surface area analysis as outlined above and/or a particle size distribution median value (D50 or d(0.5)) of not more than 10 μm, preferably of not more than 9 μm, when the isolated Letermovir pursuant to the present invention is subjected to a particle size distribution analysis as outlined above.

The expression "suitable for use in solid oral dosage forms" with the context of the amorphous Letermovir of the instant invention means that the isolated amorphous Letermovir has a particle size distribution (PSD) median value of not more than 10 μm, preferably of not more than 9 μm and/or a specific surface area of at least 1 $m^2/g$, preferably of at least 2 $m^2/g$. Said expression further means that the amorphous Letermovir thus obtained by the isolation processes of the invention is characterized by pharmaceutically acceptable impurity contents, which means that the amorphous Letermovir thus obtained is further characterized by a mesityl oxide content of </=31 ppm, preferably of </=27 ppm, even more preferably of </=23 ppm, most preferred of </=10 ppm and/or a 3-methoxyaniline content of <20 ppm, preferably <15 ppm, more preferably <10 ppm, even more preferably <5 ppm, most preferred <1.5 ppm and/or that no residual MTBE content is present and/or that <2% residual water is present and/or that below 5000 ppm residual acetone is present and/or that below 410 ppm of residual acetonitrile is present, when said impurities are determined by its respective methods as outlined above.

In addition, the expression "suitable for use in solid oral dosage forms" also means that the amorphous Letermovir thus obtained by the isolation processes of the invention exhibits sufficient dissolution characteristics, meaning that >50% dissolution of amorphous Letermovir in 30 minutes, preferably >60% dissolution in 30 minutes, more preferably >70% dissolution in 30 minutes, even more preferably >75% dissolution in 30 minutes, even more preferably >80% dissolution in 30 minutes, even more preferably >85% dissolution in 30 minutes, most preferred >90% dissolution of amorphous Letermovir in 30 minutes is present when tested for dissolution using Ph. Eur. method 2.9.3, Apparatus 2, with a paddle speed of 50 rpm at 37.0° C.±0.5° C. in 1000 ml 0.1 N HCl/0.2% sodium lauryl sulphate medium and measuring by reverse phase HPLC at point in time 15, 30, and 45 minutes as follows:

HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention Time: 1.3 minutes
Column temperature: 40° C.
Injection volume: 20 μL
Flow rate: 1.5 ml/min
Mobile phase: Buffer pH 4.0/Acetonitrile; 55/45 v/v.

With the above context the expression "suitable for use as orally administered pharmaceuticals" as regards the above-characterized amorphous Letermovir obtainable in accordance with the instant invention means that said Letermovir as API is ready to be directly formulated in the galenic formulations of the invention, and so to be directly administrable in solid oral dosage forms that are useful in methods of treatment of viral diseases, in particular human cytomegalovirus (hereinafter HCMV) infections.

The term "pharmaceutical grade" with the context of the present invention means purity and stability of amorphous Letermovir as required by actual international standards according to ICH, FDA, and EMEA.

The term "ICH guideline(s)" within the scope of the invention denotes the International Conference on Harmonization of impurities: Guideline for residual solvents Q3C (R5). The objective of this guideline is to recommend acceptable amounts for residual solvents in pharmaceuticals for the safety of the patient. The guideline recommends use of less toxic solvents and describes levels considered to be toxicologically acceptable for some residual solvents. The guideline applies to all dosage forms and routes of administration. Higher levels of residual solvents may be acceptable in certain cases such as short term (30 days or less) or topical application.

"Direct compression" is the term used to define the process where powder blends of the drug substance and excipients are directly compressed on a tablet machine. There is no mechanical treatment of the powder apart from a mixing process. The most obvious advantage of direct compression is its simplicity and subsequent economy.

In accordance with the invention the "drying", or "the drying step" can be conducted by drying using a conical dryer, a drum dryer or any other suitable technique known to the person skilled in the art.

The expression "particle size" of a particle to be determined denotes in accordance with the invention the diameter of an equivalent particle, which is believed that it is spherical and that it has the same light scattering pattern as the particle to be determined. According to the invention the particle size is determined by laser diffractometry. Particularly, for determination of the particle size a Mastersizer 2000 by Malvern Instruments is used in accordance with the invention.

According to the invention, the "D50 value" or the "d(0.5) value" of the particle size distribution describes the particle size at which 50 volume % of the particles have a smaller particle size than the particle size which corresponds to the D50 value (d(0.5)). This also means that 50% by volume of the particles have a larger particle size than the D50 value (d(0.5)). Accordingly, the D90 value (d(0.9)) of the particle size distribution is defined as the particle size at the 90 volume % of the particles have a smaller particle size than the particle size which corresponds to the D90 value (d(0.9)). Similarly, the D10 value (d(0.1)) of the particle size distribution is defined, in which 10% by volume of the particles have a smaller particle size than the particle size which corresponds to the D10 value(d(0.1)).

In accordance with the invention the "excipients" applied in the solid pharmaceutical formulations do have the function as outlined in table 1 below:

TABLE 1

| Excipient/Function | |
|---|---|
| Excipient | Function |
| microcrystalline cellulose | filler/binder |
| colloidal anhydrous silica | glidant |
| polyvinylpyrrolidon | polymer/binder |
| croscarmellose sodium | disintegrating agent |
| magnesium stearate | lubricant |
| polyethylenglycol | plasticiser |
| hypromellose | film-forming agent |
| titanium oxide | colour pigment |
| iron oxide yellow | colour pigment |
| purified water | processing agent |

ABBREVIATIONS

Throughout the specification the following abbreviations apply:

"API" denotes active pharmaceutical ingredient

"MTBE" denotes Methyl tert-butyl ether, also known as methyl tertiary butyl ether, is an organic compound with molecular formula $(CH_3)_3COCH_3$. MTBE is a volatile, flammable, and colorless liquid that is not readily soluble in water.

"DMF" denotes dimethylformamide.
"DMSO" denotes dimethyl sulfoxide.
"NMP" denotes N-methyl-2-pyrrolidone.
"MEK" denotes methyl ethyl ketone.
"THF" denotes tetrahydrofuran.
"XRPD" denotes X Ray Powder Diffraction.
"CMV" denotes cytomegalovirus.
"Ph. Eur." denotes European Pharmacopoeia, which is a pharmacopoeia, listing a wide range of active substances and excipients used to prepare pharmaceutical products in Europe. The monographs give quality standards for all the main medicines used in Europe. All medicines sold in the 36 Member States of the European Pharmacopoeia must comply with these quality standards so that consumers have a guarantee for products obtained from pharmacies and other legal suppliers.

"Ph. Eur. method 2.9.3" denotes a dissolution test for solid dosage forms. The test is used to determine the dissolution rate of the active ingredients of solid dosage forms (for example, tablets, capsules and suppositories).

"Ph. Eur. method 2.5.12" denotes water semi-micro determination according to 01/2005:20512 of the European Pharmacopoeia 5.0. The test is used to determine the water content of the API Letermovir in the amorphous state.

"IPC" denotes In Process Control.

"SCDT" denotes (2S,3S)-2,3-bis [(4-methylbenzoyl)oxy] succinic acid-methyl{(4S)-8-fluoro-2-[4-(3-methoxyphenyl)piperazin-1-yl]-3-[2-methoxy-5-(trifluoromethyl)phenyl]-3,4-dihydrochinazolin-4-yl}acetate (1:1).

"PSD" denotes particle size distribution
"SSA" denotes specific surface area
"BET" denotes Brunauer-Emmett-Teller method in terms of specific surface area analysis

EXAMPLES

1) Formulation of Amorphous Letermovir with L-Arginine

Initial formulation development studies for oral dosage forms of amorphous Letermovir with L-Arginine were conducted. The purpose of the L-Arginine in the formulation of amorphous Letermovir is to increase the dissolution properties and thus bioavailability of the drug substance.

Several trial batches were prepared with the L-Arginine granulation formulation as shown in table 2.

TABLE 2

| Formulation of dissolution trials with L-arginine | | | | | |
|---|---|---|---|---|---|
| | Batch | | | | |
| | 1 | 2 | 3 | 4 | 5 |
| Batch size (doses) | 100 | 100 | 200 | 333 | 333 |
| Ingredient | Formulation [mg/dose] | | | | |
| Letermovir | 120 | 120 | 120 | 120 | 120 |
| L-Arginine | 80 | 80 | 40 | 80 | 80 |
| Hypromellose (Methocel E5 Premium LV) | — | — | — | 112.5 | 225 |
| Water | 1500 | 750 | 750 | 750 | 1500 |
| Total (solids) | 200 | 200 | 160 | 312.5 | 425 |

First, dissolution studies were performed in order to investigate a suitable preparation process and formulation for the Letermovir granulation solution. In the next trials, the process settings for a high shear granulation were explored. As this resulted in tablet batches with long disintegration times and slow release profiles, the investigation was shifted to fluid bed granulation process. It became apparent that, surprisingly and unexpectedly, this did not result in an improvement of dissolution properties of the formulation.

1 a) Results

The dissolution behavior of the Letermovir in trials 1 to 3 with L-Arginine was not ideal due to the poor wettability of the drug substance. Letermovir floated on the surface of the solution. Furthermore, the solution foamed to a small extent and turned slightly yellow.

The dissolution times in pH 1.0+0.2% SDS for these three trials were:
1) 22 minutes
2) 37 minutes
3) >2 hours (complete dissolution after 2 days), respectively.

The viscosity of the solutions of trials 1 to 3 increased after complete dissolution. There were no wettability issues during the dissolution of the Letermovir in the L-Arginine/hypromellose solutions in trials 4 and 5. Due to the higher viscosity of the solution, the Letermovir was mixed into the solution without floating onto the surface. Due to the foaming and air entrapment in the solution it was not possible to assess the dissolution duration of the drug substance in these trials. When the solutions were left standing for 12 hours, it was observed that clear solutions (slightly yellow) were obtained.

1 b) Conclusion

The first three dissolution trials proved that Letermovir has poor wettability properties in water. In addition, the dissolution time of Letermovir in water depends on the amount of L-Arginine and (as expected) its concentration in water.

By increasing the aqueous viscosity with hypromellose, the wettability problems of Letermovir were solved. The drug substance did not float onto the surface of the solution and was mixed into the solution immediately. However, due to foaming and air entrapment into the resulting solution the dissolution time of amorphous Letermovir could not be assessed.

Further trials showed that the concentration of amorphous Letermovir in the solution could be increased from 16% (120 mg/dose Letermovir in 750 mg/dose water) to 24% (120 mg/dose Letermovir in 500 mg/dose water). Furthermore, the amounts of L-Arginine and hypromellose/hydroxypropyl cellulose in the formulation could be decreased. No significant difference in solubility behavior of Letermovir was observed in the hypromellose and hydroxypropyl cellulose solutions. Both solutions were used in subsequent granulation experiments.

The granulation process was problematic. As the amount of granulation liquid was relatively high in order to dissolve all the Letermovir the granulation was split in three steps, in order to avoid the risk of overwetting the substrate. As a result of repeated granulation and drying the hardness of the resulting granules after drying was very high, this prevented milling of the granules. Manual compression of the resulting tablets yielded tablets of adequate hardness. However, the tablets did not disintegrate within 30 minutes, and the dissolution of the tablets in pH 1.0+0.2% SDS was too slow.

In order to reduce the amount of the required granulation solution, ethanol and acetone was used as co-solvents for the granulation fluid. However, use of acetone conferred no significant processing advantage compared to water. Attempts to eliminate multiple drying and granulation steps by increasing the colloidal anhydrous silica in the formulation were also unsuccessful.

A fluid bed granulation process was employed to eliminate the multiple granulation and drying steps required for high shear granulation of Letermovir. Granulation was achieved without major issues and was well under control. The resulting trial batches contained different amounts of disintegrants, however all three batches revealed disintegration times (in water) in the range of 12 to 15 minutes. These disintegration times were shorter than the disintegration times of the trial batches prepared with high shear granulation and the dissolution was slower when compared to the high shear granulated trial batches.

1 c) Overall Conclusion for L-Arginine Formulations of Amorphous Letermovir

The lab-scale development of a formulation for Letermovir with L-Arginine did not result in a process and product with the desired properties. The dissolution of the prepared trial batches was too slow for an immediate release drug product. Subsequent attempts to improve dissolution by processing using high shear granulation and by fluid bed granulation were not successful. The L-Arginine did not appear to have a positive effect on the dissolution properties of Letermovir. It is therefore not expected that the incorporation of L-Arginine into solid formulations have positive effects on the bioavailability of Letermovir.

2) Letermovir Solubility

The inventors conducted a solubility study of amorphous Letermovir to investigate its biopharmaceutical status by standardized measures. The inventors orientated on the guidelines of the established Biopharmaceutics Classification System (BCS).

The BCS system broadly allows the prediction of the rate-limiting step in the intestinal absorption process following oral administration (cf. Arik Dahan et al., *Prediction of Solubility and Permeability Class Membership: Provisional BCS Classification of the World's Top Oral Drugs*. The AAPS Journal, Vol. 11, No. 4, December 2009 DOI: 10.1208/s12248-009-9144-x).

The solubility class boundary according to the BCS is based on the highest dose strength of the IR product. By using the BCS approach the equilibrium solubility of amorphous Letermovir under physiological pH conditions is determined. The pH-solubility profile of amorphous Letermovir was determined at 37±1° C. in aqueous media with a pH in the range of 1-7.5. A sufficient number of pH conditions were evaluated to accurately define the pH-solubility profile of amorphous Letermovir. The number of pH conditions for the solubility determination was based on the ionization characteristics of Letermovir. A minimum of three replicate determinations of solubility in each pH condition was conducted.

In detail:

The highest dose of Letermovir is exemplarily 240 mg. When dissolved in 250 ml this equates to a concentration of 0.96 mg/ml. The solubility of Letermovir was determined at 37° C.±1° C. in standard buffer solutions after stirring for 24 hours according to the FDA—Guidance for Industry, Waiver of In Vivo Bioavailability and Bioequivalence Studies for Immediate-Release Solid Oral Dosage Forms Based on a Biopharmaceutics Classification System.

TABLE 3

Letermovir solubility over the pH range 1 to 7.5.

| pH | Letermovir solubility (mg/ml) |
|---|---|
| 1 | >0.9 |
| 2.9 ($pKa_1 - 1$) | 0.8 |
| 3.9 ($pKa_1$) | 0.4 |
| 4.9 ($pKa_1 + 1$) | 0.4 |
| 7.5 | >1.0 |

Letermovir solubility data are reported in Table 3 that confirm that Letermovir cannot be considered a highly soluble drug substance. As shown in Table 3, the solubility of Letermovir over the pH-range of 1 to 7.5 varied from 0.4 to >1 mg/ml. This data reflects the challenges to be met for the provision of an amorphous API Letermovir in an orally administrable IR tablet formulation.

3) Isolation of the Amorphous Letermovir

For later tabletting of orally administrable formulations of amorphous Letermovir, at first place the API had to be isolated in solid amorphous form from an organic solution. In addition, the API has to be dried without any harm to its physical and chemical properties leading to a residual solvent content required by the current ICH guidelines.

3 a) Isolation by Roller Drying

A vacuum roller dryer (GMF Gouda, Type VT2/4.75) was used to obtain amorphous Letermovir in pharmaceutical grade. The roller dryer had the following specifications:
Roller diameter: 0.2 m
Roller length: 0.475 m
Heating surface: 0.6 m$^2$
Temperature: 40-65° C., preferably 60° C.
Pressure: 200 mbar In detail:

Acetone containing 30% Letermovir was injected by approximately 1.2 kg/h via an adjustable slit (best performance at 0.15 mm). From 9.8 kg initial acetone solution 2.35 kg solid amorphous Letermovir could be obtained. The residual acetone content was between 1.7 to 3%; however, following a subsequent drying step in e.g. a vacuum dryer or conical dryer the remaining acetone could be decreased to <0.5%.

The specific surface area of this product was <1 m$^2$/g and yielded sufficient tablet quality only by applying wet granulation process.

In the following exemplary formulation of the invention amorphous Letermovir isolated by roller drying and further processed by wet granulation showed sufficient dissolution in accordance with the invention, i.e. >50% within 30 minutes.

TABLE 4

Exemplary formulation for roller-dried amorphous Letermovir

| | mg/dose |
|---|---|
| Material-Granulate (wet) | |
| Letermovir (roller dried) | 30.00 |
| microcrystalline cellulose | 28.00 |
| colloidal anhydrous silica | 0.500 |
| povidone 25 | 2.500 |
| purified water | 25.00 |
| Sum granulate | 61.00 |
| Material-Final Blend | |
| Wet granulate | 61.00 |
| microcrystalline cellulose | 8.50 |
| colloidal anhydrous silica | 1.00 |
| Magnesium stearate | 0.75 |
| Sum final blend | 75.00 |

3 b) Isolation by Precipitation

A mixture of (2S 3S)-2,3-bis [(4-methylbenzoyl)oxy]succininc acid-{(4S)-8-fluoro-2-[4-(3-methoxyphenyl)piperazin-1-yl]-3-[2-methoxy-5-(trifluoromethyl)phenyl]-3,4-dihydroquinazolin-4-yl}acetic acid methyl ester (1:1-salt) (30.8 kg), sodium hydrogen carbonate (16.4 kg) and water (315 L) is stirred with MTBE (160 L). The phases obtained are separated and the organic phase is treated with 35 L of a 7% sodium hydrogen carbonate solution. The phases obtained are separated again and the organic phase is treated with 125 L of a 4% sodium hydroxide solution. The mixture is heated under reflux conditions. The solvent is distilled to run dry. The residual content of the reactor is stirred for further 5 h at 55-60° C. To the mixture MTBE (160 L) and water (65 L) is added under stirring at 22° C. The phases obtained are separated again and the organic phase is extracted with the aid of a 6% aqueous sodium chloride solution (30 L). The aqueous phases are reunited and stirred with water (25 L) and MTBE (160 L). The pH is adjusted to 6.5 with the aid of 1N muriatic acid. The organic phase is separated, the solvent is gently distilled to run dry and the residue is dissolved in acetone (approximately 75 L). A change of the solvent is conducted towards acetone by means of 6 distillation steps of 130 L each. The product is subsequently precipitated by adding the residual solvent (approximately 60 L) under stirring conditions (61 rpm) in an excess of water (492 L) at room temperature. Followed by centrifugation, the isolated product is dried in a vacuum dryer equipped with a spiral crumbling roller at 40 to 80° C. By this procedure a yield of 16.5 kg of (S)-{8-fluoro-2-[4-(3-methoxyphenyl)piperazin-1-yl]-3-(2-methoxy-5-trifluormethylphenyl)-3,4-dihydroquinazolin-4-yl}acetic acid is obtained as amorphous compound corresponding to 96.4% in theory.

$^1$H NMR (300 MHz, d$_6$-DMSO): δ=7.53 (d, $^2$J=8.4, 1H), 7.41 (brs, 1H), 7.22 (d, $^2$J=8.5, 1H), 7.09-7.01 (m, 2H), 6.86 (m, 2H), 6.45 (dd, $^2$J=8.2, $^3$J=1.8, 1H), 6.39-6.34 (m, 2H), 4.87 (t, $^2$J=7.3, 1H), 3.79 (brs, 3H), 3.68 (s, 3H), 3.50-3.38 (m, 4H), 2.96-2.75 (m, 5H), 2.45-2.40 (m, 1H) ppm; MS (API-ES-neg.): m/z=571 [(M-H), 100%];

Selecting the appropriate distillation conditions prior to actual isolation can minimize a potential residual MTBE and mesityl oxide content. In order to prevent self-condensation of acetone to mesityl oxide, the temperature during the solvent exchange should be kept as low as possible by applying vacuum (200 mbar) for the distillation steps.

Particularly, complete drying of the acetone-moist Letermovir in vacuum results in values <0.5% according to pharmaceutical grade (ICH guidelines) and residual water content of <2%. The API Letermovir remains in an amorphous form exhibiting a specific surface area of 1.2-2 m$^2$/g.

Those properties allow for direct use for tablet formulation using dry granulation by roller compaction.

3 c) Influence of Organic Solvents on the Precipitation of Letermovir

Influence of the organic solvents on the precipitation of Letermovir was investigated.

All results described herein are based on relevant laboratory experiments.

The solvent exchange and precipitation procedure was simulated employing readily available amorphous API Letermovir and five different solvents under investigation.

The particular choice of organic solvents for this study was based upon the following requirements:

A specific selection of structurally non-related solvents was applied to provide a broader picture. Solvents had to be water-miscible to readily fit into the process of precipitation. Only process relevant solvents were investigated, i.e. those exhibiting acceptable toxicity, high volatility and low costs. Thus, high boiling solvents such as DMF, DMSO, NMP, etc. or highly toxic ones such as glyme (1,2-dimethoxy ethane) were ruled-out for this study.

The respective solvents to be investigated were methanol, ethanol, tetrahydrofurane (THF), methyl ethyl ketone (MEK; 2-butanone), and acetonitrile (ACN).

A sample of Letermovir (dose strength 5 g) was dissolved in MTBE (26.5 ml). The solvent each was distilled off at 1 atm at 60° C. Solvent (13.5 ml) was added and distilled off at reduced pressure (200 mbar) at a maximum temperature of 40° C. Then solvent was replenished (21.5 ml) and the distillation was repeated. Said step was conducted for five times, after which another 10 ml of solvent was added. At ambient temperature this solution was added with stirring within 30 min to water (160 ml, reverse-osmosis quality), upon which the product precipitated. The suspension was stirred for another hour, the solid isolated by filtration, washed two times with water (5 ml each, reverse-osmosis quality), and dried in a vacuum oven at 45° C. for 24 h.

A first intermediate sample was taken after this period of time and drying was continued for another 63 h in order to investigate long term influences. Then the material was probed for a second time.

For analysis HPLC-purity and residual solvent content (RCS) was determined by

Gradient reverse phase HPLC-purity:

| | |
|---|---|
| Apparatus: | HPLC-system with UV-detection |
| Column: | Prodigy ODS III, 3 µm; 150 × 3.0 mm |
| Mobile Phase A: | 0.7 mL ortho-phosphoric acid 85% are added to 1.36 g Potassium phosphate monobasic and dissolved with water to 1000.0 mL |
| Mobile Phase B: | Acetonitrile |
| Flow rate: | 0.5 mL/min |
| Gradient: | 0 min 20% B |
| | 40 min 45% B |
| | 50 min 80% B |
| | 65 min 80% B |
| | 70 min 20% B |
| | 75 min 20% B |
| Detection: | UV-detection 210 nm, band width 4 nm |
| Temperature: | 55° C. |
| Injection volume: | 3 µl |
| Autosampler temperature: | 5° C. |
| Duration of the analysis: | 75 min | and static headspace gas chromatography:

| | |
|---|---|
| Apparatus | Gas Chromatograph, e.g. Agilent 6890 |
| Column | DB-WAXetr: 30 m length, 0.32 mm inner diameter, 1 µm thickness of film |
| Carrier gas, flow rate | Nitrogen, 0.9 mL/min (constant flow) 120 kPa vial pressure at the headspace sampler |
| Injector temperature | 250° C. |
| Split flow rate | 4.5 mL/min |
| Detector/temperature | FID/250° C. |
| Burning gases: | |
| Hydrogen | 40 mL/min |
| Air | 450 mL/min |
| Make-up gas (N₂) | 25 mL/min |
| Oven temperature program: | |
| Starting temperature | 40° C. |
| Holding time | 8 min |
| Heating rate | 20K/min |
| Final temperature | 70° C. |
| Holding time | 3 min |
| Cooling rate | 20K/min |
| Final temperature | 50° C. |
| Holding time | 3 min |
| Heating rate | 15K/min |
| Final temperature | 220° C. |
| Holding time | 3 min |
| Period of analysis | 30.8 min |
| Equipment | Headspace Autosampler, e.g. G1888 |
| Sample temperature | 100° C. |
| Needle temperature | 220° C. |
| Transfer temperature | 230° C. |
| GC cycle time | 40 min |
| Equilibration time | 30 min |
| Equilibration time before the 1st run | 1 min |
| Number of extractions | 1 |
| Shaking during equilibration time | 1 (slow) |
| Valve times | Pressurization time 0.25 min |
| | Loop fill time 0.20 min |
| | Loop equilibration time 0.05 min |
| | Inject time 0.50 min |
| Injections volume | 1 mL |

Results of 3 c)

Following this isolation process all solvents except MEK (vide infra) performed basically similar precipitation, filtration, washing.

In terms of chiral purity in all cases no differences were noticeable with respect to the starting material. Therefore, this study focused on purity and residual solvent properties. The results of the physical trials are summarized in below Table 5.

TABLE 5

Physical trials of precipitated Letermovir in terms of HPLC-purity and residual solvent content (RCS)

| Entry | Solvent | Yield Letermovir | HPLC purity 1[1] | RSC 1[2] | HPLC Purity 2[1] | RSC 2[2] | remarks |
|---|---|---|---|---|---|---|---|
| 1 | (Acetone) | —[3] | 99.76% | (123) | — | — | Starting material |
| 2 | MeOH | 90% | 99.87% | 10 | 99.87% | 10 | |
| 3 | EtOH | 91% | 99.38% 0.52% | 7 | 99.70% 0.23% | 3 | |
| 4 | THF | 87% | 99.54% 0.35% | >30,000 | 99.55% 0.36% | >20,000 | |
| 5 | MEK | 78% | 99.82% | >20,000 | 99.80% | >10,000 | Sticky precipitate |
| 6 | ACN | 91% | 99.91% | 34 | 99.93% | 4 | |
| 7 | Acetone | 92% | 99.88 | 3516 | 99.87 | 1247 | Reference Exp. |

[1]The first value in the cell represents the purity of Letermovir in HPLC; impurities featuring percentages greater than or equal to 0.10% are listed below the Letermovir-value.
[2]Residual solvent content (RSC) amount in ppm. Limits in ppm: methanol: 3,000; ethanol: 5,000; THF: 720; MEK: 5,000; ACN: 410; Acetone: 5,000 pursuant to ICH guidelines.
[3]The yield of this production batch is omitted since the process starts from (2S,3S)-2,3-bis[(4-methylbenzoyl)oxy]succinicacid-methyl{(4S)-8-fluoro-2-[4-(3-methoxyphenyl)piperazin-1-yl]-3-[2-methoxy-5-(trifluoromethyl)phenyl]-3,4-dihydrochinazolin-4-yl}acetate (1:1) (SCDT).

In more detail:

3 d) Methanol as Organic Solvent

In principle methanol can be used for the precipitation step, but from independent experiments it became evident that re-esterification can occur under stress conditions (elevated temperature) with lower alcohols like methanol or ethanol.

3 e) Ethanol as Organic Solvent

Ethanol did yield a by-product, which was surprisingly diminished during drying, however not in its entirety. Since the nature of this by-product is unknown, the reason for this presumed "reversibility" is not discussed here.

As with methanol the presence of ethanol in the final product was negligible with only 7 and 3 ppm after prolonged drying, respectively.

3 f) THF as Organic Solvent

THF also did yield an unknown impurity in about 0.35%, which proved stable in content under drying conditions.

On top of that residual THF proved very hard to remove: the amount exceeded the limit of 720 ppm at least 30 times, leaving a residual amount of greater than 20,000 ppm 3 g) MEK as Organic Solvent MEK on the other hand did provide for a very acceptable HPLC-purity, but it was found also not fit for process: the precipitate is sticky, thereby potentially rendering filtration difficult on a technical scale. As regards the residual solvent analysis, MEK is basically as inapplicable as THF: a residual solvent level significantly greater than 10,000 ppm (after extensive drying) exceeds the limit of 5,000 ppm at least by a factor of two. THF, this solvent is to be considered not suitable.

3 h) Acetonitrile as Organic Solvent

Acetonitrile did not pose any problems. Although its toxicity and thus strict limits (410 ppm) could give rise to concerns about residual solvents, determined amounts were well below 410 ppm already after one day of drying and just slipped through the quantification limit of 5 ppm after an additional 63 h (amount: 4 ppm).

All these data were in favor of acetonitrile, but from independent experiments it became obvious that under influence of bases and elevated temperature some racemization could be observed in this solvent.

3 i) Acetone as Organic Solvent

As a surprising finding, the water-soluble acetone, however, provided for the best results in terms of isolation properties for Letermovir. Acetone did not affect the quality of Letermovir at all and could be removed by drying far below the 0.5% threshold pursuant to ICH guidelines, resulting in a product, which directly could be used for oral and i.v. formulation (water for injection was used for the precipitation step in order to provide the API Letermovir for i.v. formulations).

With respect to the results as mentioned above, the utilization of acetone provides for several advantages:
high volatility, thus reasonably easy to remove;
low toxicity, thus acceptable levels of the residual solvent are present;
non-reactive towards the API Letermovir and therefore, virtually no by-products are present.

3 j) Summary and Conclusion

Under laboratory conditions among the solvents tested ethanol, THF and MEK proved not suitable either for quality or process reasons. Although methanol and acetonitrile yielded positive results in terms of HPLC-purity, they are not recommended: potential side reactions are re-esterification and racemization, respectively.

Although acetonitrile would make for a good substitute, acetone is from toxicological and economical aspects still preferred as organic solvent for precipitation of the API Letermovir in accordance with the present invention.

4) Galenic Formulations/Tabletting Methods

The inventors found the following galenic formulations and methods of processing suitable to formulate the amorphous Letermovir in immediate release formulations.

The excipients, which were used and its function is described in table 6:

TABLE 6

| Excipient/Function for galenic formulations | |
|---|---|
| Excipient | Function |
| microcrystalline cellulose | filler/binder |
| colloidal anhydrous silica | glidant |
| povidone 25 | polymer/binder |
| croscarmellose sodium | disintegrating agent |
| Magnesium stearate | lubricant |
| ethanol | processing agent |
| acetone | processing agent |
| purified water | processing agent |

To prove immediate release formulation dissolution testing is performed using Ph. Eur. 2.9.3, Apparatus 2, with a paddle speed of 50 rpm. The proposed dissolution method is summarized below. A reverse phase HPLC method is used for analyzing samples.

Dissolution Apparatus Operating Conditions:
Equipment: Ph. Eur. 2.9.3 Apparatus 2 (Paddle)
Sample size: 6 tablets
Temperature: 37.0° C.±0.5° C.
Rotation speed: 50 rpm
Medium: 0.1 N HCl/0.2% sodium lauryl sulfate
Medium volume: 1000 ml
Sampling volume 1 ml
Sampling times: 15, 30, and 45 minutes HPLC Operating Conditions:
Column: Waters Symmetry Nucleosil 100 C18, 40 mm×4.0 mm, 10 μm
Detection wavelength: 256 nm
Approximate runtime: 4 minutes
Approximate retention Time: 1.3 minutes
Column temperature: 40° C.
Injection volume: 20 μL
Flow rate: 1.5 ml/min
Mobile phase: Buffer pH 4.0/Acetonitrile; 55/45 v/v Assay and Related Substances A gradient reverse phase HPLC assay method is used to determine the drug product identification, assay and degradation products.

Operating Conditions:
Column: Intertsil ODS III 5 μm or equivalent
Solvent Acetonitrile/0.1 N HCl; 3+7 (v/v)
Eluent A: Water, pH 2.40; B: Acetonitrile
Detection wavelength: 235 nm
Column temperature: 40° C.
Injection volume: 15 μL
Flow rate: 1.0 ml/min
Run time: 30 minutes 4 a) Wet Granulations of Roller-Dried and Precipitated Amorphous Letermovir High shear wet granulation with purified water as processing agent resulted in the formation of a good granulate where the material was completely bound, soft and voluminous. High shear wet granulation was possible with both the roller dried and precipitated API when water was used as the processing agent. The quantitive formulation of the high shear wet granulations of roller-dried and precipitated amorphous Letermovir is reported in Table 7.

TABLE 7

Formulation for high shear wet granulations of roller-dried and precipitated Letermovir

|  | mg/dose |
|---|---|
| Material-Granulate (wet) | |
| Letermovir (roller dried or precipitated) | 30.00 |
| microcrystalline cellulose | 28.00 |
| colloidal anhydrous silica | 0.50 |
| povidone 25 | 2.50 |
| purified water | 25.00 |
| Sum granulate | 61.00 |
| Material-Final Blend | |
| Wet granulate | 61.00 |
| microcrystalline cellulose | 10.00 |
| croscarmellose sodium | 2.25 |
| colloidal anhydrous silica | 1.00 |
| Magnesium stearate | 0.75 |
| Sum final blend | 75.00 |

The granules incorporating the precipitated Letermovir (40311P18) appeared visually more robust than the granules incorporating the roller dried Letermovir (40311P17). The granules incorporating the roller dried Letermovir appeared to flow more freely than the granules incorporating the precipitated Letermovir. This apparent difference in powder flow resulted in higher variation observed in the measured compression force during manufacture of the tablets when compressing the granules containing the precipitated Letermovir. This difference in compression force variability resulted in the tablets containing the roller dried Letermovir granules exhibiting more uniform tablet weight and thickness (reported in table 8 and table 9).

TABLE 8

IPC results roller dried (40311P17) versus precipitated (40311P18) Letermovir

|  |  | Actual value | |
|---|---|---|---|
| Physical parameters | Nominal value | 40311P17 | 40311P18 |
| Average mass [mg] | 75 ± 3% (73-77) | 75 | 81 |
| Min. mass [mg] | | 68 | 69 |
| Max. mass [mg] | | 82 | 91 |
| Diameter [mm] | 5.4-5.6 | 5.5 | 5.5 |
| Height [mm] | determine | 3.0-3.1 | 2.9-3.3 |
| Hardness [N] | determine | 100 | 117 |
| Friability [%] | ≤1.0 | 0.2 | 0.2 |
| Disintegration in H₂0 [min] | ≤30 | 10'30-13'15 | 20'00-23'30 |

The tablets containing the roller dried Letermovir (40311P17) exhibited faster dissolution (reported in Table 9).

TABLE 9

Dissolution results roller dried (40311P17) versus precipitated (40311P18) Letermovir

|  | 40311P17 | | 40311P18 | |
|---|---|---|---|---|
| Time [min] | Ø Dissolution [%] | Srel [%] | Dissolution [%] | Srel [%] |
| 15 | 64 | 19.8 | 24 | 19.1 |
| 30 | 95 | 2.1 | 82* | 9.1 |
| 45 | 96 | 2.5 | 104 | 6.8 |
| 60 | 97 | 2.0 | 107 | 7.1 |

*remark: single values 68%, 87%, 88%, 88%, 79%, 82%

Conclusion to 4a)

A granulation of both isolated Letermovir types with a purified water/povidone solution as processing agent was possible. The tablets manufactured from the roller dried Letermovir granulate were more uniform in thickness and weight than the tablets manufactured from the precipitated Letermovir granulate when processed by high shear wet granulation. In addition, the dissolution of the tablets containing roller dried Letermovir exhibited faster dissolution up to 30 minutes than the tablets containing precipitated Letermovir.

4 b) Roller Dried Letermovir

The inventors also tested roller dried Letermovir only. The amount of disintegrating agent croscarmellose sodium was increased from 3% to 5% in order to promote disintegration of the tablet and reduce the dissolution variability. The amount of microcrystalline cellulose was decreased accordingly to maintain the tablet weight. The quantitative formulation is reported in Table 10.

TABLE 10

Exemplary formulation of roller dried Letermovir with increased croscarmellose sodium

|  | mg/dose |
|---|---|
| Material-Granulate (wet) | |
| Letermovir (roller dried) | 30.00 |
| microcrystalline cellulose | 28.00 |
| colloidal anhydrous silica | 0.50 |
| povidone 25 | 2.50 |
| purified water | 25.00 |
| Sum granulate | 61.00 |
| Material-Final Blend | |
| Wet granulate | 61.00 |
| microcrystalline cellulose | 8.50 |
| croscarmellose sodium | 3.75 |
| colloidal anhydrous silica | 1.00 |
| Magnesium stearate | 0.75 |
| Sum final blend | 75.00 |

Results to 4 b):

Granulation and tabletting were performed without problems and IPC (In Process Control) data is reported in tables 11 and 12.

TABLE 11

IPC data for roller dried Letermovir as wet granulation in a formulation with increased croscarmellose sodium

| Physical parameters | Nominal value | Actual value |
| --- | --- | --- |
| Average mass [mg] | 75 ± 3% (73-77) | 74 |
| Min. mass [mg], | 68 | 71 |
| Max. mass [mg] | 82 | 81 |
| Diameter [mm] | 5.4-5.6 | 5.5 |
| Height [mm] | determine | 3.0-3.1 |
| Hardness [N] | determine | 87 |
| Friability [%] | ≤1.0 | 0.1 |
| Disintegration in $H_2O$ [min] | ≤30 | 14'00-16'20 |

TABLE 12

Dissolution data for roller dried Letermovir as wet granulation in a formulation with increased croscarmellose sodium

| Time [min] | Ø Dissolution [%] | Srel [%] |
| --- | --- | --- |
| 15 | 72 | 10.7 |
| 30 | 99 | 1.3 |
| 45 | 99 | 1.3 |
| 60 | 100 | 1.4 |

Conclusion:

All IPC results and the dissolution results were according to the specification as shown in Table 21. The standard deviation of approx. 1.3% after 30 min, 45 min and 60 min was pharmaceutically acceptable.

5) Dry Granulations of Roller-Dried and Precipitated Amorphous Letermovir

In parallel to the wet granulation trials also dry granulation trials were performed using a Kilian rotary press to compress the isolated Letermovir into compacts followed by milling of the compacts using a conical mill using the formulation reported in Table 13.

TABLE 13

Exemplary formulation of dry granulated Letermovir

|  | mg/dose |
| --- | --- |
| Material-Granulate (dry) |  |
| Letermovir (roller dried) | 30.00 |
| microcrystalline cellulose | 18.00 |
| colloidal anhydrous silica | 0.50 |
| povidone 25 | 2.50 |
| Magnesium stearate | 0.30 |
| Sum granulate | 51.30 |
| Material-Final Blend |  |
| dry granulate | 51.30 |
| microcrystalline cellulose | 20.00 |
| croscarmellose sodium | 2.25 |
| colloidal anhydrous silica | 1.00 |
| Magnesium stearate | 0.45 |
| Sum final blend | 75.00 |

Results to 5):

The dry granulation, crushing of the dry granulates and preparation of final blend was possible at small scale. All the IPC results were according to the specification and are reported in Table 14:

TABLE 14

IPC data for the exemplary dry granulation of Letermovir

| Physical parameters | Nominal value | Actual value |
| --- | --- | --- |
| Average mass [mg] | 75 ± 3% (73-77) | 75 |
| Min. mass [mg], | 68 | 69 |
| Max. mass [mg] | 82 | 83 |
| Diameter [mm] | 5.4-5.6 | 5.5 |
| Height [mm] | determine | 3.0-3.1 |
| Hardness [N] | determine | 92 |
| Friability [%] | ≤1.0 | 0.2 |
| Disintegration in $H_2O$ [min] | ≤30 | 9'40-17'20 |

But dissolution data was below 80% at 30 minutes as reported in Table 15:

TABLE 15

Dissolution data for the exemplary dry granulation of Letermovir

| Time [min] | Ø Dissolution [%] | Srel [%] |
| --- | --- | --- |
| 15 | 35 | 43.3 |
| 30 | 73 | 16.1 |
| 45 | 103 | 3.4 |
| 60 | 106 | 4.3 |

Conclusion:

Manufacture using dry granulation was possible with this formulation at a small scale. The dissolution result was below the target specification. In addition the standard deviation of the 15-minute point in time was very high, which suggests that the dissolution rate may be limited by the initial disintegration of the tablet. To promote the disintegration of the tablets the amount of croscarmellose sodium was also increased from 3% to 5% and the microcrystalline cellulose amount was decreased accordingly to maintain the tablet weight. Increasing of the quantity of the disintegration agent croscarmellose sodium resulted also in faster dissolution of the cores as already shown above for wet granulations. The results are according to the specification. The dissolution was further improved where the disintegrants was incorporated within the dry granulate.

6) Dry Granulation—Roller Dried API Versus Precipitated API

Trials were conducted to evaluate if dry granulation was possible with both, the roller dried and precipitated Letermovir. The quantitative formulation is reported in Table 16.

TABLE 16

Dry granulation formulation of roller dried and precipitated Letermovir

|  | mg/dose |
| --- | --- |
| Material-Granulate (dry) |  |
| Letermovir (roller dried; precipitated) | 30.00 |
| microcrystalline cellulose | 16.50 |
| colloidal anhydrous silica | 0.50 |
| povidone 25 | 2.50 |
| croscarmellose sodium | 1.50 |
| Magnesium stearate | 0.30 |
| Sum granulate | 51.30 |
| Material-Final Blend |  |
| dry granulate | 51.30 |
| microcrystalline cellulose | 20.00 |
| croscarmellose sodium | 2.25 |

TABLE 16-continued

Dry granulation formulation of roller dried and precipitated Letermovir

|  | mg/dose |
|---|---|
| colloidal anhydrous silica | 1.00 |
| Magnesium stearate | 0.45 |
| Sum final blend | 75.00 |

The dry granulation, crushing of the dry granulates and preparation of final blends was performed without problems using both, the roller dried (40311P15) and precipitated (40311P16) Letermovir. The granules incorporating the precipitated Letermovir appeared to flow more freely granules incorporating the roller dried Letermovir. This difference in powder flow was reflected in higher variation in the observed compression force during manufacture of the tablets when compressing the granules containing the precipitated Letermovir. This resulted in the tablets containing the precipitated Letermovir granules exhibiting more uniform tablet weight and thickness. For details see corresponding IPC data in Table 17.

TABLE 17

IPC data dry granulation formulation of roller dried (40311P15) and precipitated (40311P16) Letermovir

|  |  | Actual value | |
|---|---|---|---|
| Physical parameters | Nominal value | 40311P15 | 40311P16 |
| Avgerage mass [mg] | 75 ± 3% (73-77) | 80 | 74 |
| Min. mass [mg], | 68 | 75 | 69 |
| Max. mass [mg] | 82 | 87 | 78 |
| Diameter [mm] | 5.4-5.6 | 5.5 | 5.5 |
| Height [mm] | determine | 3.0-3.3 | 2.9-3.0 |
| Hardness [N] | determine | 93 | 92 |
| Friability [%] | ≤1.0 | 0.1 | 0.2 |
| Disintegration in H$_2$0 [min] | ≤30 | 9'00-13'00 | 10'00-13'20 |

The corresponding dissolution results are shown in Table 18.

TABLE 18

Dissolution results; dry granulation formulation of roller dried (40311P15) and precipitated (40311P16) Letermovir

|  | 40311P15 | | 40311P16 | |
|---|---|---|---|---|
| Time [min] | Ø Dissolution [%] | Srel [%] | Ø Dissolution [%] | Srel [%] |
| 15 | 60 | 8.2 | 50 | 14.3 |
| 30 | 100 | 1.8 | 89 | 2.2 |
| 45 | 102 | 1.3 | 91 | 2.6 |
| 60 | 102 | 1.3 | 93 | 2.0 |

Overall Conclusion

Initial development trials began by investigating processing using wet granulation and dry granulation. Initial attempts to perform high shear wet granulation using organic solvents were unsuccessful. However, by using water as the processing agent, the granulation was improved.

Manufacturing by using dry granulation is preferable to wet granulation as the dry granulation process is not batch size limited and would be expected to be easier to scale up reproducibly. The dissolution rate can be increased by promoting disintegration of the tablet through increasing the quantity of disintegrating agent in the formulation. The highest effects were shown by addition of intragranular disintegrants.

Trials with two types of amorphous Letermovir, which were manufactured using two different processes, namely roller dried Letermovir and precipitated Letermovir were conducted. During several trials it was found out that the roller dried API was more useful for the wet granulation technology and the precipitated API was more useful for the dry granulation technology. With both technologies 30 mg tablets with acceptable physical parameters according to the specification and an adequate dissolution were manufactured.

In addition one trial with dry granulation technology with the highest dose strength in the homologous series was manufactured successfully. The physical data and the dissolution were acceptable for all dose strengths.

7) Exemplary Formulations of Four Dose Strengths Pursuant to the Invention for Precipitated API

TABLE 19

Exemplary formulations for the dose strengths 30 mg, 60 mg, 120 mg, and 240 mg Letermovir

| Material | 30 mg strength [mg/dose] | 60 mg strength [mg/dose] | 120 mg strength [mg/dose] | 240 mg strength [mg/dose] |
|---|---|---|---|---|
| Dry Granulate | — | — | — | — |
| Letermovir | 30.000 | 60.000 | 120.000 | 240.000 |
| Cellulose, microcrystalline | 16.500 | 33.000 | 66.000 | 132.00 |
| Silica, colloidal anhydrous | 0.500 | 1.000 | 2.000 | 4.000 |
| Povidone 25 | 2.500 | 5.000 | 10.000 | 20.000 |
| Croscarmellose Sodium | 1.500 | 3.000 | 6.000 | 12.00 |
| Magnesiumstearate | 0.300 | 0.600 | 1.200 | 2.400 |
| Sum Granulate | 51.300 | 102.600 | 205.200 | 410.400 |
| Final blend/tablet | — | — | — | — |
| Granulate | 51.300 | 102.600 | 205.200 | 410.400 |
| Cellulose, microcrystalline | 20.000 | 40.000 | 80.000 | 160.000 |
| Croscarmellose Sodium | 2.250 | 4.500 | 9.000 | 18.000 |
| Silica, colloidal anhydrous | 1.000 | 2.000 | 4.000 | 8.000 |
| Magnesium stearate | 0.450 | 0.900 | 1.800 | 3.600 |
| Sum Final blend/tablet | 75.000 | 150.000 | 30.000 | 600.00 |
| Film coated tablet | — | — | — | — |
| Macrogol 6000 | 0.460 | 0.900 | 1.800 | 3.600 |
| Hypromellose | 1.380 | 2.700 | 5.400 | 10.800 |
| Water purified* | 14.310 | 28.000 | 56.000 | 112.000 |
| Titanium dioxide | 0.370 | 0.720 | 1.440 | 2.880 |
| Iron oxide yellow | 0.090 | 0.180 | 0.360 | 0.720 |
| Water purified* | 6.389 | 12.500 | 25.000 | 50.000 |
| Film coated Tablet | 77.30 | 154.500 | 309.000 | 618.000 |

8) Roller Compactor for Dry Granulation of Precipitated Letermovir

Subsequently the dry granulation process was transferred to a roller compactor. Roller compaction is a more scalable process for dry granulation than compression of compacts with milling that was used for the initial feasibility batches. The powder flow was also improved by using the Gerteis Minipactor® roller compactor when compared to dry granulation using tabletting machine (slugging) and milling. The formulation was optimized further by use of a coarser grade of microcrystalline cellulose. The "initial" and "optimized" formulations are shown in table 20 below.

TABLE 20

Optimized formulations of precipitated Letermovir as dry granulation roller compaction

| Component | Type "initial" formulation" | Type "optimised" formulation" | mg/dose |
|---|---|---|---|
| Letermovir | precipitated | precipitated | 30.00 |
| Microcrystalline Cellulose | Emcocel 50M | Emcocel 50M | 16.50 |
| Silica, colloidal anhydrous | Cab o Sil Fumed Silica grade M-5P | Cab o Sil Fumed Silica grade M-5P | 0.50 |
| Povidone | Polyvinylpyrrolidon | Polyvinylpyrrolidon | 2.50 |
| Croscarmellose Sodium | Ac-Di Sol | Ac-Di Sol | 1.50 |
| Magnesium Stearate | MF-2_V vegetable | MF-2_V vegetable | 0.30 |
| Dry granulate | — | — | 51.30 |
| Microcrystalline Cellulose | Emcocel 50M | Avicel PH200 | 20.00 |
| Croscarmellose Sodium | Ac-Di Sol | Ac-Di Sol | 2.25 |
| Silica, colloidal anhydrous | Cab o Sil Fumed Silica grade M-5P | Cab o Sil Fumed Silica grade M-5P | 1.00 |
| Magnesium Stearate | MF-2_V vegetable | MF-2_V vegetable | 0.45 |
| Core | — | — | 75.00 |

Results to 8):

Up Scaling of the dry granulations process to a batch size of 12 kg was subsequently achieved without negative influence on compression characteristics. The content uniformity of the samples taken in the beginning, the middle and end of the tabletting process of the 60 mg dose strength tablets and a representative sample of the 240 mg dose strength tablet exhibited good homogeneity of Letermovir within the tablet blend. The dissolution results of all tablets strengths were acceptable.

9) Proposed Shelf-Life Specification of Amorphous Letermovir in Tablet Formulation

TABLE 21

Proposed specifications and test methods for Letermovir tablets

| Test | Specification | Test Method |
|---|---|---|
| Appearance | Yellow/ochre, round tablets without tablet markings | Visual |
| Identification | The retention time (HPLC) of Letermovir must comply with the reference sample. | RP-HPLC Method |
| Identification | Spectra comparable to the reference material | FT-IR |
| Potency Assay | 90.0-110.0% | RP-HPLC Method |
| Individual Unspecified Impurities | NMT 0.2% | |
| Specified Impurities | NMT 0.2% | |
| Total Impurities Products | NMT 3.0% | |
| Dissolution | Q = 80% in 30 minutes | Ph. Eur. method 2.9.3 USP <711> |
| Uniformity of Dosage Units | Complies | PhEur 2.9.40> |
| Water Content | Report Results | PhEur 2.5.12 |
| Microbial Enumeration | | |
| Total Aerobic Microbial Count: | NMT 1000 cfu/g | USP <61> |
| Total Combined Yeasts and Molds: | NMT 100 cfu/g | USP <62> |
| Absence of *Escherichia coli* | NMT 100 cfu/g | Ph. Eur. 2.6.12, 2.6.13 |

NMT = Not more than

10) Long-term Stability

Long-term stability studies were conducted with testing of color, dissolution, degradation products and assay at regular intervals to confirm the stability of amorphous Letermovir precipitate tablets.

The analytical methods used in these studies are reported in Table 21. In addition, disintegration, water content and hardness/breaking load were conducted as informative tests.

Samples of one batch of each dose strength of Letermovir precipitate tablets, packaged in 45 ml HDPE bottles with child-resistant closures were stored at 25° C./60% relative humidity and at 40° C./75% relative humidity. Stability data after 36 months storage were reported.

Additional forced degradation studies were conducted. One batch per dose strength of Letermovir was stored at 60° C. for 3 months. In order to assess the hydrolytic stability, one batch of the 20 mg dose strength was stored with open storage at 40° C./75% relative humidity for 3 months.

Conclusion for Stability Study

Throughout the study duration (36 months), all tested parameters (i.e. appearance, dissolution, degradation products and assay) complied with the shelf-life specification. Letermovir is stable under long-term storage conditions (25° C./60% relative humidity and under accelerated storage conditions (40° C./75% relative humidity); no significant changes were observed. Only a slight increase (of max. 0.2%) in degradation products was detected. The largest single degradation product remained below 0.5%. Representative stability data is reported in the Tables of FIG. 8: a); b); c).

As the data available after 36 months stability studies (real time data at 25° C./60% RH) fully comply with the shelf life specifications, and given that there was no significant increase of degradation products, no evidence for crystallization during the storage period or any other negative change in quality occurred, a shelf-life of 36 months was assigned for both tested dose strengths.

11) Absolute Bioavailability of Letermovir in the Amorphous State

Pharmacokinetic Objectives in Cohort 1 of a Clinical Trial:

Assessment of absolute bioavailability after oral administration of 30 mg Letermovir in the amorphous state versus a 30 minute intravenous administration of 30 mg Letermovir in 150 ml saline solution 0.9%.

Design

Cohort 1 of the trial was conducted in an open-label, randomized (to treatment sequence), single center crossover design (2 periods) in 12 healthy female subjects. Subjects received a single intravenous dose of 30 mg Letermovir via a 30-minute infusion in one period ("reference") and a single oral dose of 30 mg Letermovir in the amorphous state in the other period ("test"). In both periods subjects were in-house from Day −1 to Day 4 (72 h after dosing on Day 1). The washout period between the periods (i.e. the dosing) was at least one week. The 30 mg dose in Cohort 1 was evaluated (see FIGS. 7a and 7b).

Methods

Plasma concentrations of Letermovir were determined using a lower limit of quantification (LLOQ) of 1.00 ng/mL. Pharmacokinetic parameters $AUC_{0-\infty}$, $C_{max}$, F, $AUC_{0-last}$, $t_{max}$, λZ, $t_{1/2z}$, CL/F, CL, Vd/F, Vd, MRT, $AUC_{0-\infty}/D$, $C_{max}/D$, $AUC_{0-last}/D$ for Cohort 1 were calculated in Win-Nonlin using the actual sampling times. Descriptive statistics were calculated for the plasma concentrations and for the derived pharmacokinetic parameters. Statistics included sample size (n), mean, standard deviation (SD), percentage of coefficient of variation (% CV), geometric mean, median, minimum, and maximum. In Cohort 1, absolute bioavailability of Letermovir was explored statistically, by comparing log transformed $AUC_{0-last}$ and $AUC_{0-\infty}$ values for oral Letermovir in the amorphous state (test) and intravenous Letermovir (reference), using linear mixed effects modeling. Only paired observations were included in the statistical analysis.

Pharmacokinetic Results:

See FIGS. 7a and 7b.

Conclusions:

After a single 30 mg oral and intravenous (30 min infusion) dose of Letermovir, based on statistical analysis of $AUC_{0-last}$, the absolute bioavailability of Letermovir was 76%.

12) BET Specific Surface Area Analysis

BET specific surface area analysis was conducted on various batches of precipitated amorphous Letermovir. The same was done on a batch of Letermovir (named BXR3GBL) produced according to Example 11 of WO 2006/133822. The results of the analysis are shown below in Table 22:

TABLE 22

| BET specific surface area analysis | |
| --- | --- |
| Batch number or identification name of Letermovir | Specific Surface Area (SSA), m²/g; BET value on average |
| Precipitated Letermovir (Trial number) | |
| 40475297 | 1.25 |
| 40474375 | 1.46 |
| 40483517 | 1.87 |
| 40474463 | 1.23 |
| 40483515 | 1.03 |
| 40483516 | 1.28 |
| 40479189 | 1.26 |
| 40479463 | 1.45 |
| 40479248 | 1.45 |
| 40479434 | 1.48 |
| 40479198 | 2.09 |
| 40483517 | 1.83 |
| 40479198 | 2.25 |
| 40479200 | 1.30 |
| 40479326 | 1.76 |
| 40479201 | 1.97 |
| 40479202 | 1.69 |
| Amorphous Letermovir-Example 11 of WO 2006/133822 | BET value on average |
| Batch BXR3GBL | 0.64 |

It can be derived from table 22 that the batch BXR3GBL, being prepared according to prior art WO 2006/133822 has a SSA by BET value of 0.64 m²/g on average, whereas precipitated amorphous Letermovir of the invention has a SSA by BET value ranging on average from 1.03 m²/g (Trial number 40483515) to 2.25 m²/g (Trial number 40479198).

The particular BET method is characterized by the following parameter:

Principle: Nitrogen adsorption at 77 K; method according to Brunauer, Emmett and Teller (BET)
Method: volumetric method (method II) according to USP <846>
Instrument: Tristar 3000/VacPrep 061 (Micromeritics)
Sample mass: approximately 1.5-2.5 g
Sample preparation: degassing for 2 h at 40° C. under vacuum (final vacuum <2.7 Pa)
Pressure range p/p0: 0.05-0.15 (3 data points).

13) Laser Diffraction Particle Size Distribution Analysis (Mastersizer 2000)

Laser diffraction particle size distribution analysis was conducted on two batches of precipitated amorphous Letermovir of the invention and on a batch of amorphous Letermovir (referred to as BXR3GBL) produced according to Example 11 of WO 2006/133822 while using laser diffraction technique of the Mastersizer 2000 (Malvern Instruments). The results of the analysis are presented in FIG. 9(a-c) in the form of three particle size distribution charts and the numeric part of the results is shown below in Table 23:

TABLE 23

| Laser diffraction particle size distribution analysis (Mastersizer 2000) accompanied by a further BET measurement for specific surface area | | |
| --- | --- | --- |
| Batch number or identification name of Letermovir | Particle Size Median Value d(0.5), μm | Specific Surface Area (SSA), m²/g |
| Precipitated Letermovir | | |
| 1300750 | 9.383 | 2.1 |
| 1300735 | 8.880 | 2.18 |
| Letermovir-Example 11 of WO 2006/133822 | | |
| Batch BXR3GBL | 21.607 | 1.55 |

It can be derived the table 23 that the prior art batch BXR3GBL, prepared by a process according to Example 11 of WO 2006/133822 exhibits a significantly higher particle size median value than precipitated amorphous Letermovir of the invention. This indicates that the particle size distribution of BXR3GBL is remarkably higher than that of precipitated amorphous Letermovir in accordance with the invention.

The particular PSD analysis method is characterized by the following parameter:

Device: Mastersizer 2000 with dry dispersion
Modus: Fraunhofer; weight-in quantity: 0.3-0.4 g
Measurement time: 20 seconds
Background time: 6 seconds
Obscuration limits: 0.5 to 6%
Sample tray: micro volume; small sieve with balls
Feed rate: 45-55%
Dispersive pressure: 2.5 bar Four independent analyses were performed and the results were averaged.

14) Purity Determination by Gas Chromatography

Four batches of precipitated amorphous Letermovir were subjected to purity determination by gas chromatography and the same was conducted with a batch of amorphous Letermovir (referred to as BXR3GBL) produced according to Example 11 of WO 2006/133822. The results of the analysis are shown below in table 24:

TABLE 24

Purity determination by gas chromatography

| | Batch number or identification name of Letermovir | | | | |
|---|---|---|---|---|---|
| | Precipitated Letermovir | | | | Letermovir- according to Example 11 of WO 2006/ 133822 |
| Impurities | 1300698 | 1300712 | 1300735 | 1300750 | BXR3GBL |
| 2-Methoxy-5-(trifluoromethyl)-aniline | <1.5 ppm | <1.5 ppm | <1.5 ppm | <1.5 ppm | <1.5 ppm |
| 3-Methoxyaniline | <1.5 ppm | <1.5 ppm | <1.5 ppm | <1.5 ppm | 10 ppm |
| Bis-(2-chloroethyl)-amine | <1.5 ppm | <1.5 ppm | <1.5 ppm | <1.5 ppm | <1.5 ppm |
| Mesityl oxide | 9 ppm | 23 ppm | 31 ppm | 27 ppm | 240 ppm |
| 2-Methoxy-5-(trifluoromethyl)-isocyanate | — | — | — | — | 35 ppm |

It can be derived from table 24 that the prior art batch BXR3GBL, which was prepared according to Example 11 of WO 2006/133822 shows significantly increased contents of toxic impurities compared to precipitated amorphous Letermovir obtained by the methods of the present invention.

BRIEF DESCRIPTION OF THE DRAWINGS

FIG. 1: Precipitation experiments. Entry 1-3; distillative MTBE-removal with methanol, ethanol, and acetonitrile; precipitated Letermovir by addition to water. Entry 4 distillate MTBE-removal with acetone; precipitated Letermovir by addition to water. Entry 5-6; inverted precipitation: water addition to acetone and acetonitrile solution, respectively. Entry 7-11; drum-dryer simulation of roller-dried Letermovir using methanol, ethanol, acetonitrile, DCM, and MTBE as volatile solvents. $^{1)}$ indicates that the yield is diminished by material losses on the glass wall.

FIG. 4 shows a comparison between solid Letermovir (1) and solubilized Letermovir (2) in contrast to DMSO (3). In agreement with the XRPD results of FIG. 2, solid Letermovir was also confirmed to be amorphous using Raman spectroscopy.

FIG. 5-Solubility of amorphous Letermovir in water.

FIG. 6-PH solubility profile of Letermovir.

FIG. 7a Pharmacokinetic results. Absolute bioavailability of Letermovir at 30 mg sub-therapeutic dose was tested.

FIG. 7b Pharmacokinetic results. Absolute bioavailability of Letermovir at 30 mg sub-therapeutic dose was tested.

FIG. 8a—Tablet stability properties of 240 mg Letermovir were tested.

FIG. 8b—Tablet stability properties of 60 mg Letermovir were tested.

FIG. 8c—Tablet stability properties of 120 mg Letermovir were tested.

FIG. 10—Stability data for batch 10101001 of precipitated amorphous Letermovir of the invention at 25° C/60% relative humidity (long term conditions).

FIG. 11—Stability data for batch 09041001 of precipitated amorphous Letermovir of the invention at 25° C/60% relative humidity for 48months.

Figure 2:
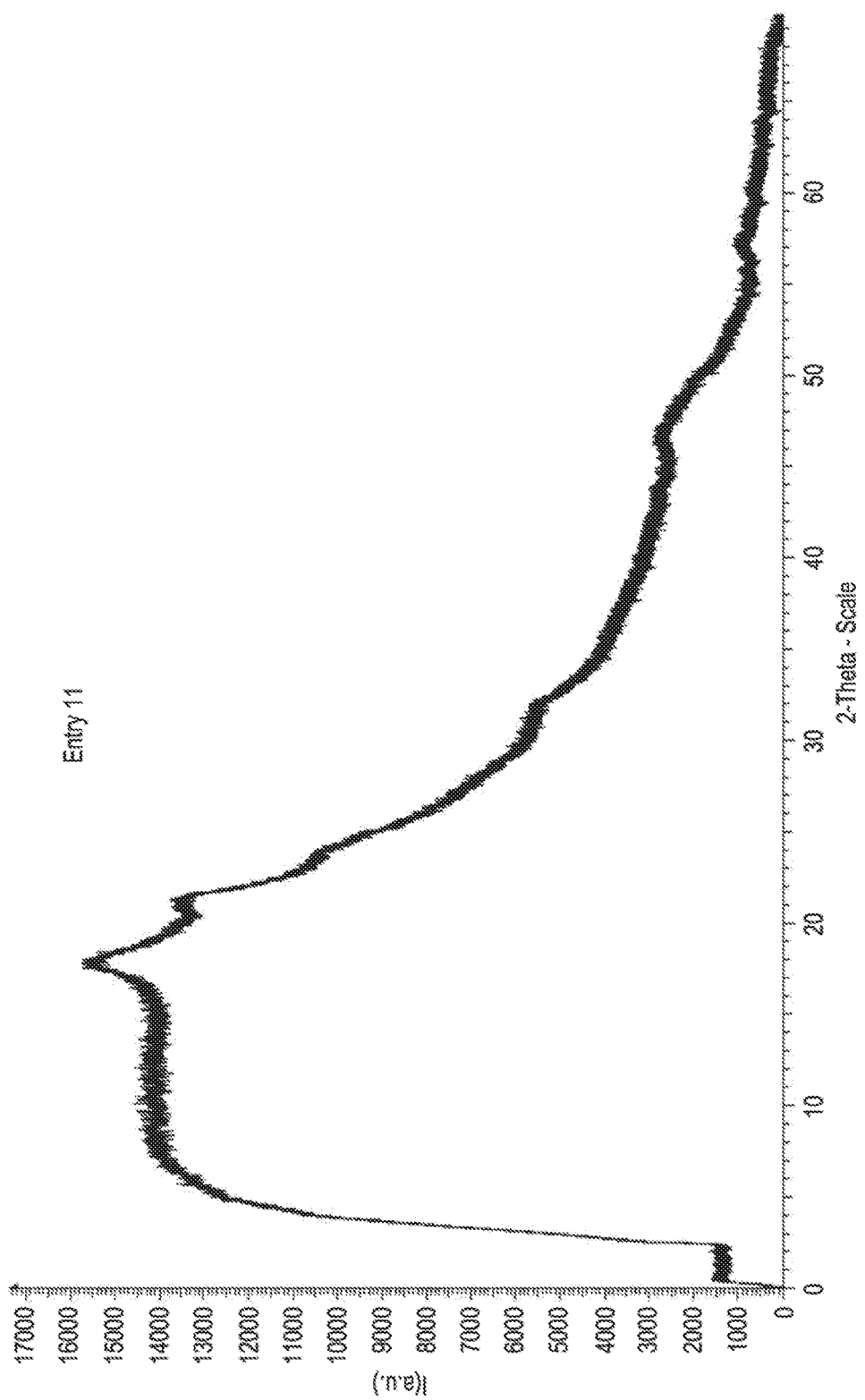
FIG. 2: XRPD diffractogram of entry 11 from FIG. 1 is shown. The sample of entry 11 was isolated by drum dryer simulation of roller-dried Letermovir using MTBE as volatile solvent. The graph is typical for an amorphous solid such as Letermovir. All other diffractograms (entries 1 through 10) are basically identical with respect to the one of entry 11. Obviously, all isolation techniques led to amorphous material (see also column "Morphology by XRPD" in FIG. 1).
Figure 3:
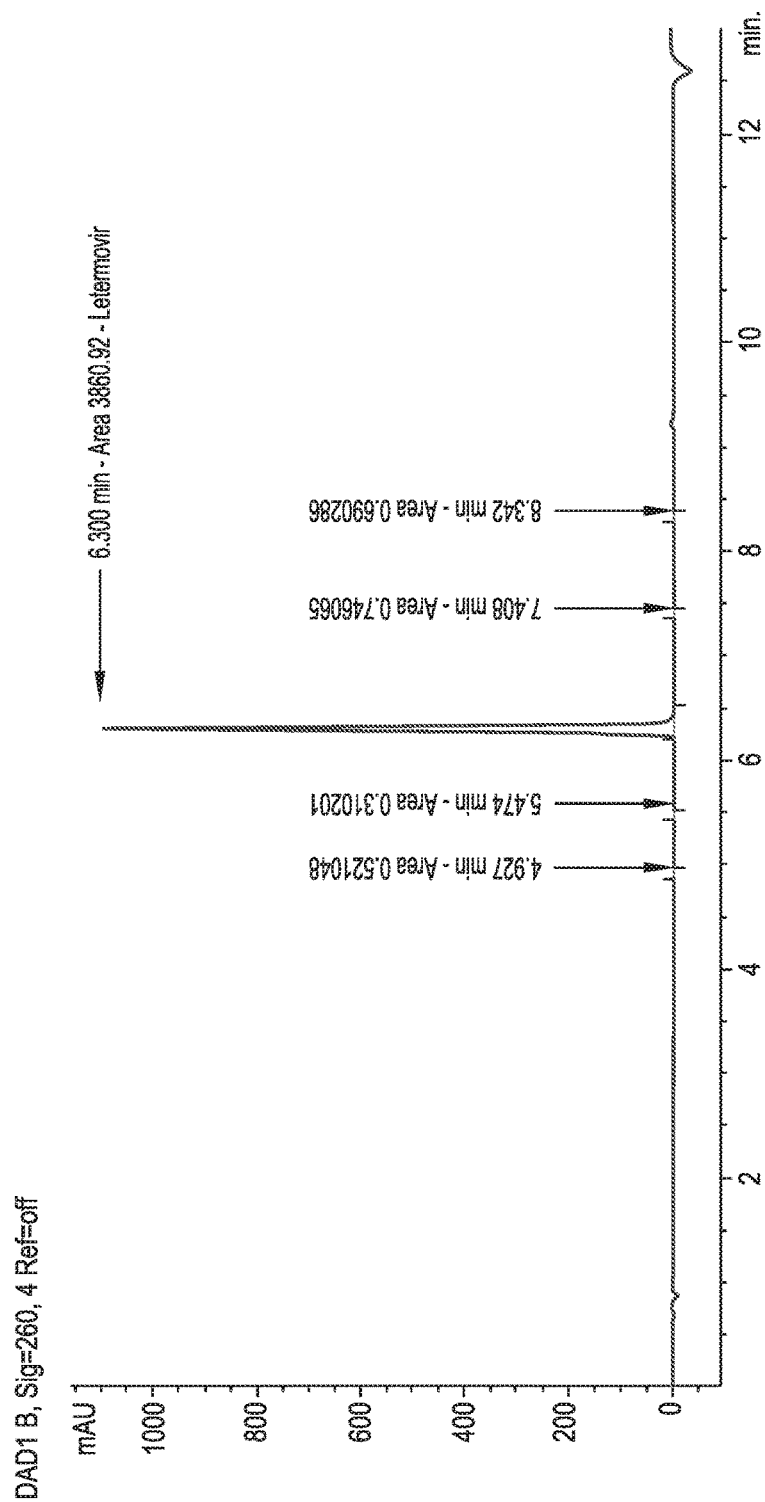
FIG. 3: HPLC chromatogram of isolated Letermovir.
Figure 4:
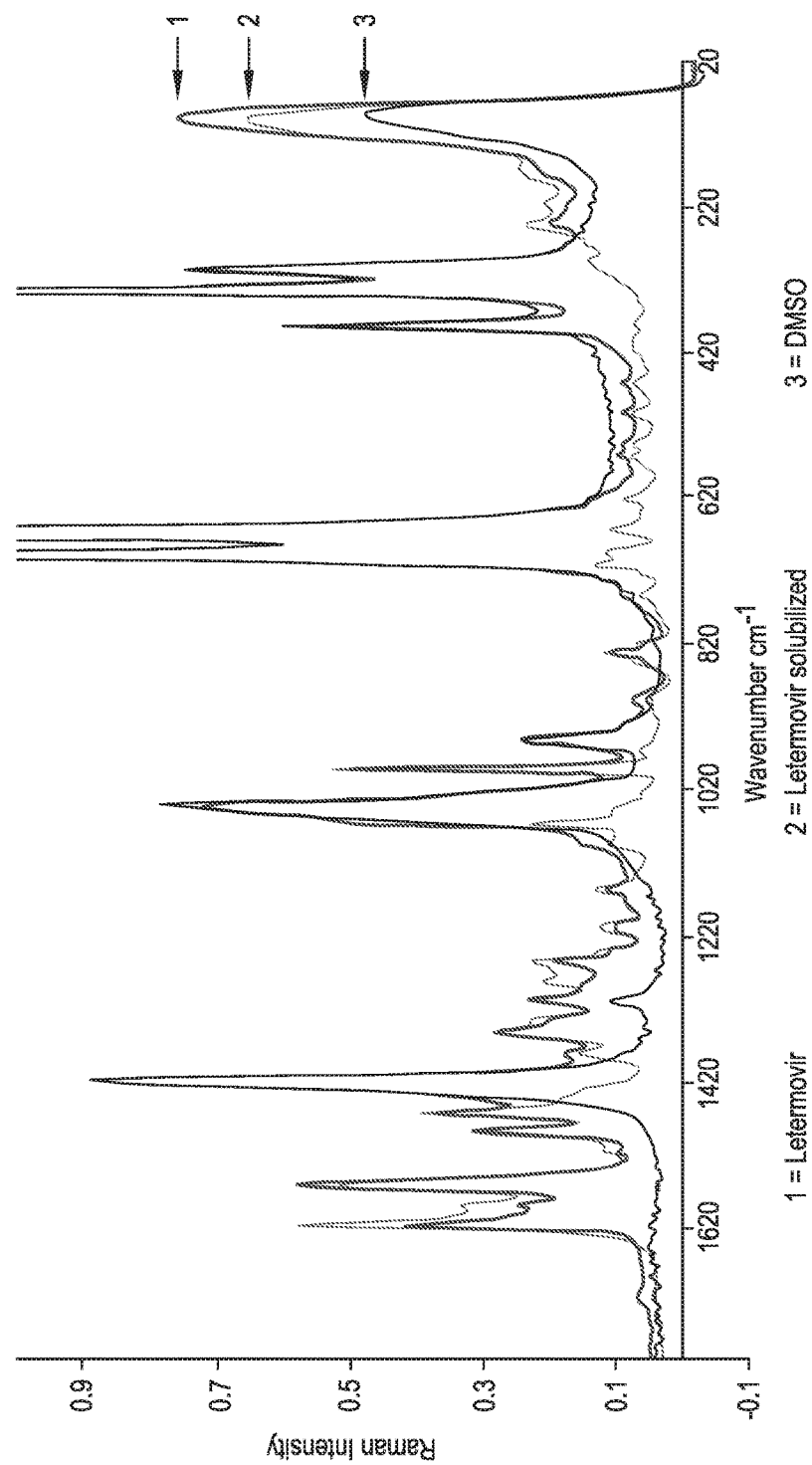
FIG. 4: Raman spectra of amorphous Letermovir. Raman spectroscopy measurements were performed in accordance with Ph. Eur. Ed. VI, using spectrometer type Bruker RFS 100/S Raman spectrometer, excitation laser power 400 mW, resolution 2 cm$^{-1}$, number of scan =128, acquisition range 3300-0 cm$^{-1}$, aperture 5.0 mm, 96 well plate glass vials, and spectrum treatment of linear baseline correction, normalization.
Figure 9A:
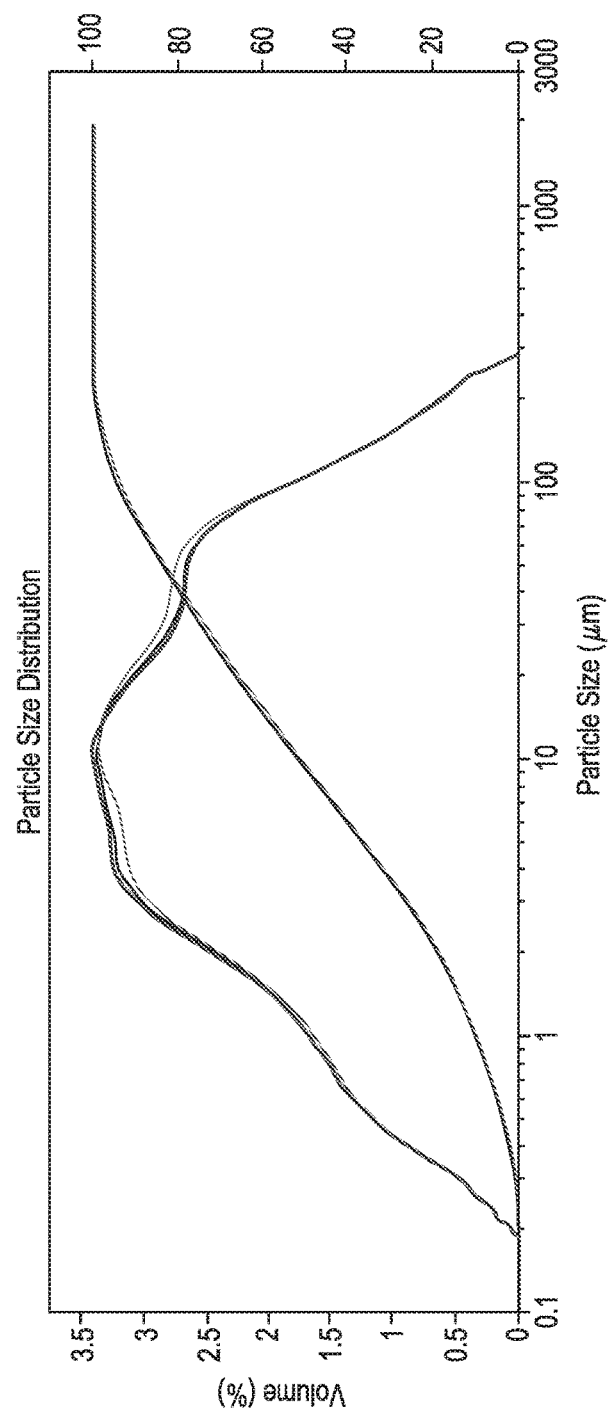
FIG. 9a—Particle size distribution chart for a batch of precipitated Letermovir in accordance with the present invention (1300750) showing different sections with a time difference of approximately 2 to 3 min.
Figure 9B:
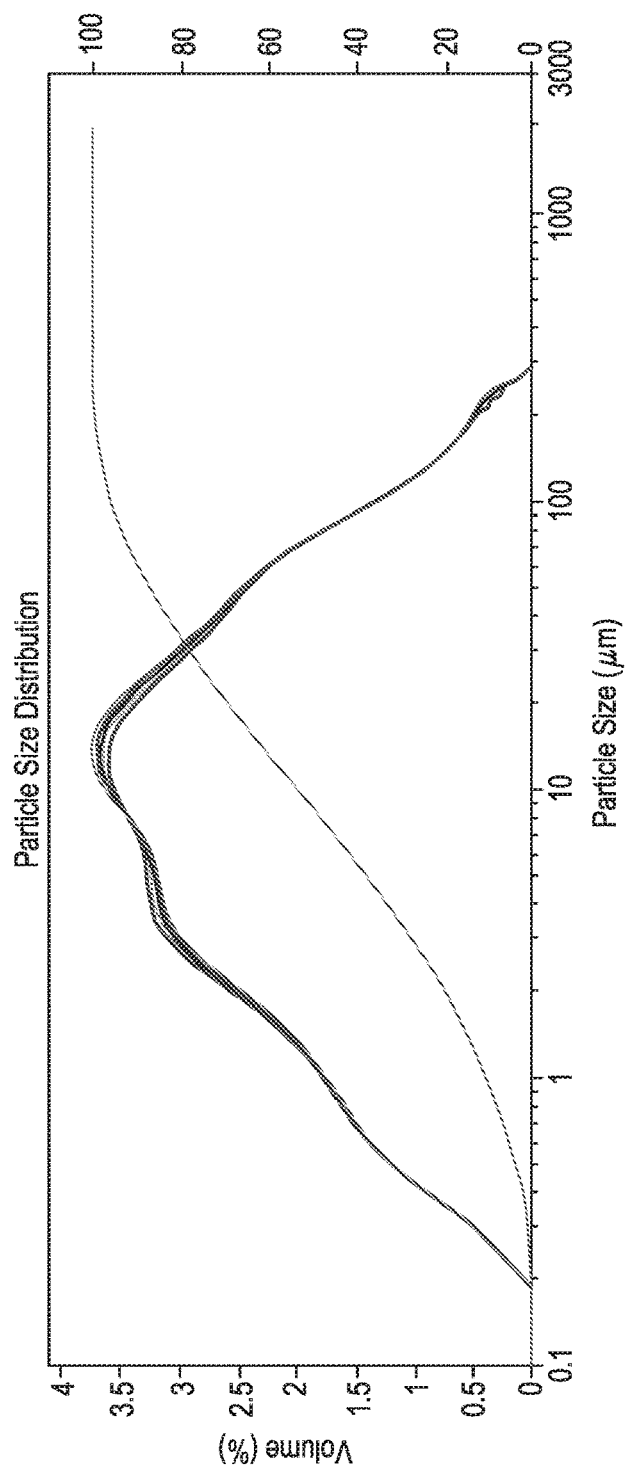
FIG. 9b—Particle size distribution chart for another batch of precipitated Letermovir in accordance with the present invention (1300735) showing different sections with a time difference below 2 min.
Figure 9C:
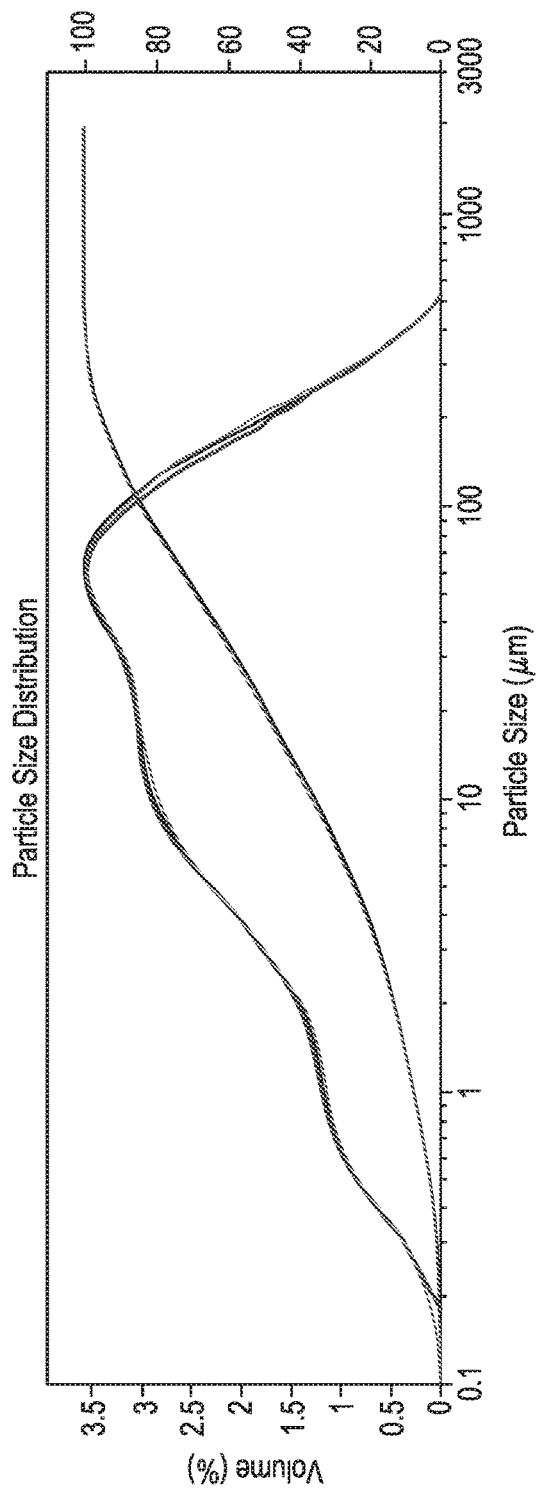
FIG. 9c—Particle size distribution chart for a batch of Letermovir (named BXR3GBL) produced according to Example 11 of WO 2006/133822 A1 showing different sections with a time difference of approximately 2 min.
Figure 12:
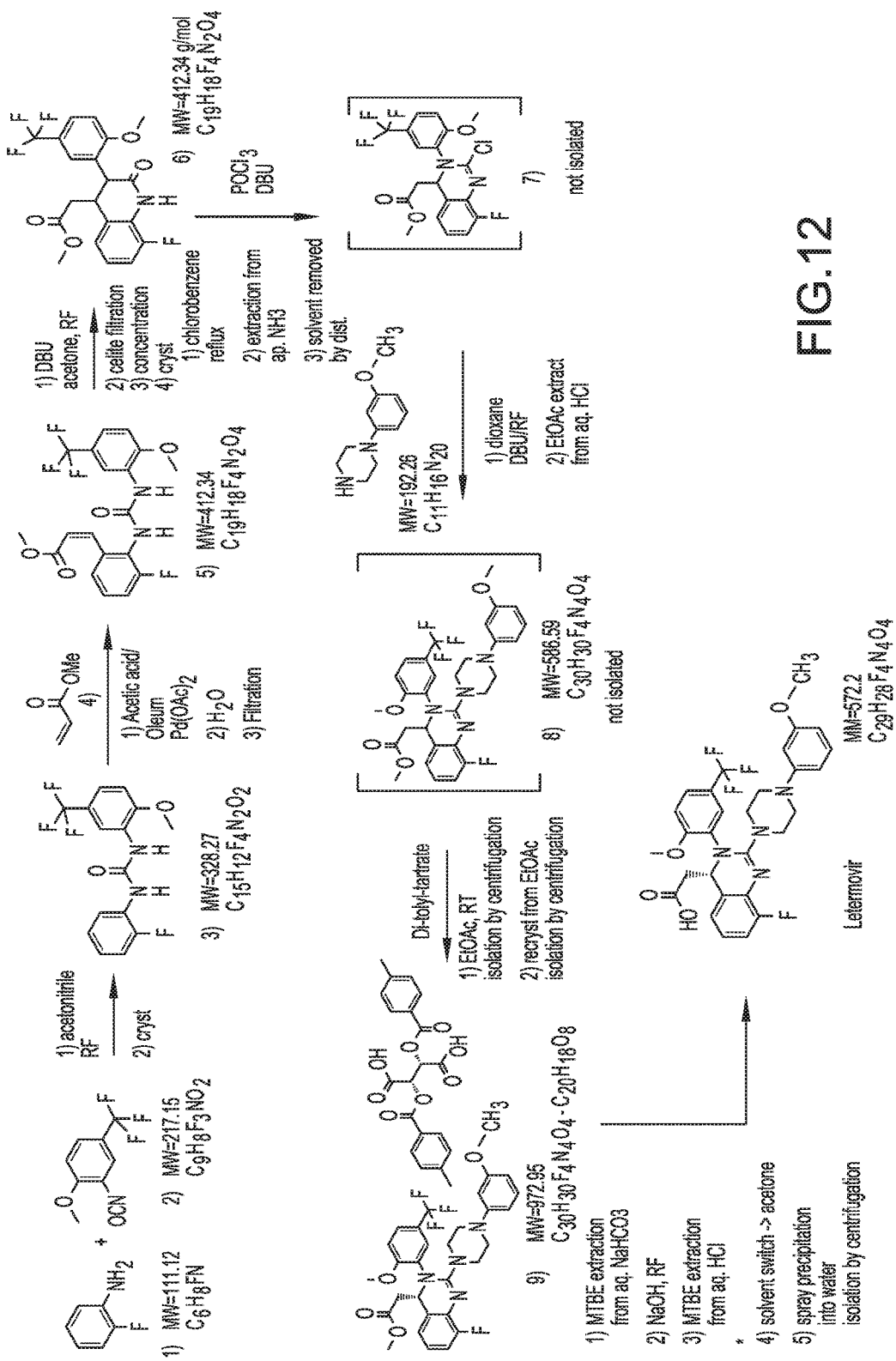
FIG. 12—Reaction scheme for the preferred synthetic route of Letermovir. Asterisk on the bottom left before step 4)—solvent switch indicates the step where the isolation pursuant to the invention initiates. Herein, the most preferred isolation method is exemplarily shown for solvent switch to acetone (4), followed by spray precipitation into water (5). Isolation by centrifugation follows.

The invention claimed is:

1. Letermovir according to Formula (I),

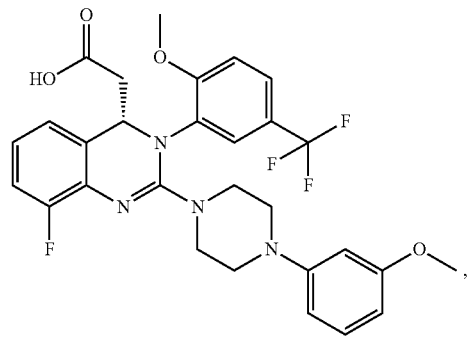

Formula (I)

which is amorphous Letermovir, the pure chemical entity with (S)-configuration, obtained by a precipitation process for isolating amorphous Letermovir, wherein the process comprises:
   precipitating said amorphous Letermovir from the water miscible solvents acetone or acetonitrile into excess stirred water,
   followed by isolating the amorphous Letermovir via filtration or centrifugation, wherein said process for isolating the amorphous Letermovir does not include precipitation using alcohols or precipitation using tetrahydrofuran or methylethylketone.

2. Letermovir according to claim 1, wherein said process for isolating amorphous Letermovir has a drying step in vacuo subsequent to the isolating.

3. Letermovir according to claim 1, wherein said process for preparing the amorphous Letermovir further comprises dry granulation processing of the amorphous Letermovir subsequent to the isolating.

4. Solid pharmaceutical formulation comprising the amorphous Letermovir according to claim 1, the pure chemical entity with (S)-configuration, wherein said solid pharmaceutical formulation is orally administrable.

5. Solid pharmaceutical formulation according to claim 4, further comprising povidone, croscarmellose sodium, microcrystalline cellulose, colloidal anhydrous silica and magnesium stearate.

6. Solid pharmaceutical formulation according to claim 5, wherein said amorphous Letermovir is in an amount of 30.0% to 50.0 % (w/w), said povidone is in an amount of 2.0% to 10.0 % (w/w), said croscarmellose sodium is in an amount of 2.0% to 10.0 % (w/w), said microcrystalline cellulose is in an amount of 20.0% to 70.0 % (w/w), said colloidal anhydrous silica is in an amount of 0.5% to 5.0 % (w/w), and said magnesium stearate is in an amount of 0.1% to 5.0 % (w/w).

7. Solid pharmaceutical formulation according to claim 4, which is effective to achieve an absolute bioavailability of 70% ±30% of Letermovir when administered orally in said formulation comprising at least 5 mg of the amorphous Letermovir.

8. Solid pharmaceutical formulation according to claim 4, wherein said solid pharmaceutical formulation is an immediate release formulation, characterized in that not less than 85% amount of the amorphous Letermovir is dissolved within 30 min using USP Apparatus I at 100 rpm or USP Apparatus II at 50 rpm in a volume of 900 ml or less of each of the following media:
(1) acidic media, such as USP simulated gastric fluid without enzymes;
(2) pH 4.5 buffer; and
(3) pH 6.8 buffer or USP-simulated intestinal fluid without enzymes.

9. Solid pharmaceutical formulation according to claim 4, wherein said amorphous Letermovir exhibits a chemical stability of at least 36 months during storage at room temperature (25° C.) and (60%) relative humidity, when determined by gradient reverse phase HPLC as follows:

HPLC Operating Conditions:
Column: Intertsil ODS III 5 μm or equivalent
Solvent Acetonitrile/0.1 N HC1; 3 +7 (v/v)
Eluent A: Water, pH 2.40; B: Acetonitrile
Detection wavelength: 235 nm
Column temperature: 40° C.
Injection volume:15 μL
Flow rate: 1.0 ml/min
Run time: 30 minutes.

10. A method for prophylaxis or treatment of a disease associated with the group of Herpesviridae, which comprises administering a solid pharmaceutical formulation according to claim 4.

11. A method according to claim 10, wherein the disease is cytomegalovirus (CMV).

12. A method according to claim 10, wherein the disease is human cytomegalovirus (HCMV).

13. A method according to claim 10, wherein the disease is selected from: HCMV infection in a subject having AIDS; HCMV-pneumonitis;
HCMV-encephalitis; gastrointestinal HCMV infection; systemic HCMV infection;
HCMV infection in a newborn or child; acute HCMV infection of a pregnant women;
HCMV infection in an immuno-suppressed cancer patient; and HCMV-mediated tumor progression in a HCMV-positive cancer patient.

14. Letermovir according to claim 1, wherein said amorphous Letermovir subjected to a Brunauer-Emmett-Teller (BET) specific surface area (SSA) analysis has BET specific surface area of at least 1 m$^2$/g.

15. Letermovir according to claim 4, wherein said amorphous Letermovir subjected to a Brunauer-Emmett-Teller (BET) specific surface area (SSA) analysis has BET specific surface area of at least 1 m$^2$/g.

16. Letermovir according to claim 1, wherein said amorphous Letermovir has a particle size distribution median value of not more than 10 μm.

17. Letermovir according to claim 4, wherein said amorphous Letermovir has a particle size distribution median value of not more than 10 μm.

18. Letermovir according to claim 1, wherein said process for isolating amorphous Letermovir consists only of filtering, centrifuging and/or drying.

* * * * *